United States Patent
Reversade et al.

(10) Patent No.: US 9,862,986 B2
(45) Date of Patent: Jan. 9, 2018

(54) MUTEINS OF THE PYRROLINE-5-CARBOXYLATE REDUCTASE 1

(71) Applicant: AGENCY FOR SCIENCE, TECHNOLOGY AND RESEARCH, Singapore (SG)

(72) Inventors: Bruno Reversade, Singapore (SG); Stefan Mundlos, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 14/583,083

(22) Filed: Dec. 24, 2014

(65) Prior Publication Data
US 2015/0240285 A1 Aug. 27, 2015

Related U.S. Application Data

(63) Continuation of application No. 13/322,750, filed as application No. PCT/IB2010/001239 on May 26, 2010.

(60) Provisional application No. 61/180,937, filed on May 26, 2009.

(51) Int. Cl.
| | |
|---|---|
| *C12Q 1/26* | (2006.01) |
| *C12N 9/06* | (2006.01) |
| *C12N 15/113* | (2010.01) |
| *C12Q 1/68* | (2006.01) |
| *G01N 33/50* | (2006.01) |
| *G01N 33/573* | (2006.01) |
| *A61K 38/00* | (2006.01) |

(52) U.S. Cl.
CPC ............ *C12Q 1/26* (2013.01); *C12N 9/0028* (2013.01); *C12N 15/1137* (2013.01); *C12Q 1/6886* (2013.01); *C12Y 105/01002* (2013.01); *G01N 33/5088* (2013.01); *G01N 33/573* (2013.01); *A61K 38/00* (2013.01); *C12N 2310/11* (2013.01); *C12N 2310/3233* (2013.01); *C12Q 2600/158* (2013.01); *G01N 2333/90661* (2013.01); *G01N 2800/20* (2013.01)

(58) Field of Classification Search
None
See application file for complete search history.

(56) References Cited

U.S. PATENT DOCUMENTS

| | | |
|---|---|---|
| 4,677,968 A | 7/1987 | Krueger |
| 5,432,272 A | 7/1995 | Benner |
| 6,127,121 A | 10/2000 | Meyer, Jr. et al. |
| 6,143,877 A | 11/2000 | Meyer et al. |
| 2002/0081691 A1 | 6/2002 | Hillman et al. |

FOREIGN PATENT DOCUMENTS

| | | |
|---|---|---|
| WO | WO 02/099043 A2 | 12/2002 |
| WO | WO 2004/078992 A2 | 9/2004 |
| WO | WO 2004/087992 A2 | 10/2004 |
| WO | WO 2007/131293 A1 | 11/2007 |

OTHER PUBLICATIONS

PCT International Search Report for PCT Counterpart Application No. PCT/IB2010/001239 containing Communication relating to the Results of the International Search Report, 5 pages, (dated Sep. 16, 2010).
PCT Written Opinion of the International Searching Authority for PCT Counterpart Application No. PCT/IB2010/001239, 8 pages, (dated Sep. 16, 2010).
PCT Notification concerning Transmittal of International Preliminary Report on Patentability (Chapter I of the Patent Cooperation Treaty) for PCT Counterpart Application No. PCT/IB2010/001239, 10 pages, (dated Dec. 8, 2011).
Swiss-Prot Accession No. Q922W5.1, 3 pages, (Mar. 1, 2005).
Swiss-Prot Accession No. Q58DT4.1, 2 pages, (Jan. 9, 2007).
GenBank Accession No. AAI66873.1, 2 pages, (Jul. 15, 2008).
GenBank Accession No. AAI23511.1, 2 pages, (Mar. 6, 2007).
Matthias R. Baumgartner, et al., "Hyperammonemia with reduced ornithine, citrulline, arginine and proline: a new inborn error caused by a mutation in the gene encoding $\Delta^1$-pyrroline-5-carboxylate synthase", Human Molecular Genetics, vol. 9, No. 19, pp. 2853-2858, (2000).
Vishwanathan Hucthagowder, et al., "*Fibulin*-4: A Novel Gene for an Autosomal Recessive Cutis Laxa Syndrome", The American Journal of Human Genetics, vol. 78, pp. 1075-1080, (2006).
Bart Loeys, et al., "Homozygosity for a missense mutation in fibulin-5 (*FBLN5*) results in a severe form of cutis laxa", Human Molecular Genetics, vol. 11, No. 18, pp. 2113-2118, (2002).

(Continued)

*Primary Examiner* — Rebecca Prouty
(74) *Attorney, Agent, or Firm* — Blakely, Sokoloff, Taylor & Zafman LLP

(57) ABSTRACT

The invention relates to muteins of the pyrroline-5-carboxylate reductase 1 (PYCR1), to nucleic acid molecules comprising a nucleotide sequence encoding such muteins, to methods of determining in a subject a predisposition of having an age related disorder associated with PYCR1, to methods of identifying a compound capable of modifying the expression of PYCR1, and methods of treating a subject having an age-related disorder associated with PYCR1. The invention further relates to a genetically modified animal and a method of modifying the expression of the PYCR1 gene in an animal.

18 Claims, 13 Drawing Sheets

(56) References Cited

OTHER PUBLICATIONS

Uwe Kornak, et al., "Impaired glycosylation and cutis laxa caused by mutations in the vesicular H+-ATPase subunit ATP6V0A2", Nature Genetics, vol. 40, No. 1, pp. 32-34, (Jan. 2008).

Hans Christian Hennies, et al., "Gerodermia osteodysplastica is caused by mutations in *SCYL1BP1*, a Rab-6 interacting golgin", Nature Genetics, vol. 40, No. 12, pp. 1410-1412, (Dec. 2008).

Man-Cong Zhang, et al., "Cutis Laxa Arising from Frameshift Mutations in Exon 30 of the Elastin Gene (ELN)", The Journal of Biological Chemistry, vol. 274, No. 2, pp. 981-986, (1999).

Bruno Reversade, et al., "Mutations in *PYCR1* cause cutis laxa with progeroid features", Nature Genetics, vol. 41, No. 9, pp. 1016-1021, (Sep. 2009).

Duane L. Guernsey, et al., "Mutation in Pyrroline-5-Carboxylate Reductase 1 Gene in Families with Cutis Laxa Type 2", The American Journal of Human Genetics, vol. 85, pp. 120-129, (Jul. 10, 2009).

Hala Megarbane, et al., "An Autosomal-Recessive Form of Cutis Laxa Is Due to Homozygous *Elastin* Mutations, and the Phenotype May Be Modified by a Heterozygous *Fibulin 5* Polymorphism", Journal of Investigative Dermatology, vol. 129, pp. 1650-1655, (2009).

L. Van Maldergem, et al., "Cobblestone-like brain dysgenesis and altered glycosylation in congenital cutis laxa, Debré type", Neurology, vol. 71, pp. 1602-1608, (2008).

George M. Martin, et al., "Genetic Modulation of Senescent Phenotypes in *Homo sapiens*", Cell, vol. 120, pp. 523-532, (Feb. 25, 2005).

Hiroshi Mitsubuchi, et al., "Inborn Errors of Proline Metabolism", The Journal of Nutrition, vol. 138, No. 10, pp. 2016S-2020S, (2008).

Louise S. Bicknell, et al., "A missense mutation in *ALDH18A1*, encoding $\Delta^1$-pyrroline-5-carboxylate synthase (P5CS), causes an autosomal recessive neurocutaneous syndrome", European Journal of Human Genetics, vol. 16, pp. 1176-1186, (2008).

Vishwanathan Hucthagowder, et al., "Loss-of-function mutations in ATP6V0A2 impair vesicular trafficking, tropoelastin secretion and cell survival", Human Molecular Genetics, vol. 18, No. 12, pp. 2149-2165, (2009).

Navasona Krishnan, et al., "Proline modulates the intracellular redox environment and protects mammalian cells against oxidative stress", Free Radical Biology and Medicine, vol. 44, No. 4, pp. 671-681, (Feb. 15, 2008).

James M. Phang, et al., "The Metabolism of Proline as Microenvironmental Stress Substrate", The Journal of Nutrition, vol. 138, No. 10, pp. 2008S-2015S, (2008).

Zhaohui Meng, et al., "Crystal Structure of Human Pyrroline-5-carboxylate Reductase", Journal of Molecular Biology, vol. 359, pp. 1364-1377, (2006).

Robert S. Balaban, et al., "Mitochondria, Oxidants, and Aging", Cell, vol. 120, pp. 483-495, (Feb. 25, 2005).

Gonçalo R. Abecasis, et al., "Merlin—rapid analysis of dense genetic maps using sparse gene flow trees", Nature Genetics, vol. 30, pp. 97-101, (Jan. 2002).

Holger Thiele, et al., "HaploPainter: a tool for drawing pedigrees with complex haplotypes", Bioinformatics, vol. 21, No. 8, pp. 1730-1732, (2005).

Carmel Hensey, et al., "Programmed Cell Death during Xenopus Development: A Spatio-temporal Analysis", Developmental Biology, vol. 203, pp. 36-48, (1998).

Leslie Picoult-Newberg, et al., "Mining SNPs From EST Databases", Genome Research, vol. 9, pp. 167-174, (1999).

David Altshuler, et al., "An SNP map of the human genome generated by reduced representation shotgun sequencing", Nature, vol. 407, pp. 513-516, (Sep. 28, 2000).

EPO Communication enclosing Extended European Search Report for European Counterpart Application No. 10780124.3, 10 pages, (May 3, 2013).

First Office Action for corresponding Chinese Patent Application No. 201080022686.4, 26 pages. (including English translation), (dated Jul. 4, 2013).

Nils Homer, et al., "BFAST: An Alignment Tool for Large Scale Genome Resequencing", PLoS One, vol. 4, No. 11, e7767, 12 pages, (Nov. 2009).

Biology Online Dictionary, "Mutein", retrieved from the Internet: http://www.biology-online.org/dictionary/Mutein, 3 pages, (retrieved on Dec. 23, 2013).

Free Online Medical Dictionary, "Mutein", retrieved from the Internet: http://medical-dictionary.thefreedictionary.com/mutein, 2 pages, (retrieved on Dec. 23, 2013).

Cay M. Kielty, "Elastic Fibres in Health and Disease", Expert Reviews in Molecular Medicine, vol. 18, No. 19, pp. 1-23, (Aug. 2006).

Emma C. Kivuva, et al., "De Barsy Syndrome: A Review of the Phenotype", Clinical Dysmorphology, vol. 17, pp. 99-107, (2008).

L.I. Al-Gazali, et al., "Gerodermia Osteodysplastica and Wrinkly Skin Syndrome: Are They the Same?", American Journal of Medical Genetics, vol. 101, pp. 213-220, (2001).

H. Hamamy, et al., "Wrinkly Skin Syndrome", Clinical and Experimental Dermatology, vol. 30, pp. 590-592, (2005).

Arti Nanda, et al., "Gerodermia Osteodysplastica/Wrinkly Skin Syndrome: Report of Three Patients and Brief Review of the Literature", Pediatric Dermatology, vol. 25, No. 1, pp. 66-71, (Jan./Feb. 2008).

J. Kunze, et al., "De Barsy Syndrome—An Autosomal Recessive, Progeroid Syndrome", European Journal of Pediatrics, vol. 144, pp. 348-354, (1985).

Anna Rajab, et al., "Geroderma Osteodysplasticum Hereditaria and Wrinkly Skin Syndrome in 22 Patients from Oman", American Journal of Medical Genetics Part A vol. 146A, pp. 965-976, (2008).

Deanna Guerra, et al., "The De Barsy Syndrome", Journal of Cutaneous Pathology, vol. 31, pp. 616-624, (2004).

Matthias R. Baumgartner, et al., "$\Delta^1$-Pyrroline-5-Carboxylate Synthase Deficiency: Neurodegeneration, Cataracts and Connective Tissue Manifestations Combined with Hyperammonaemia and Reduced Ornithine, Citrulline, Arginine and Proline", European Journal of Pediatrics, vol. 164, pp. 31-36, (2005).

Curt H. Hagedorn, et al., "Transfer of Reducing Equivalents into Mitochondria by the Interconversions of Proline and $\Delta^1$-Pyrroline-5-Carboxylate", Archives of Biochemistry and Biophysics, vol. 225, No. 1, pp. 95-101, (Aug. 1983).

A. M. De Barsy, et al., "Dwarfism, Oligophrenia and Degeneration of the Elastic Tissue in Skin and Cornea. A New Syndrome?", Helvetica Paediatrica Acta, vol. 23, Fasc. 3, pp. 305-313, (Jun. 1968).

Fig. 1A

|  10 | 20 | 30 | 40 | 50 | 60 |
|---|---|---|---|---|---|
| MSVGFIGAGQ | LAFALAKGFT | AAGVLAAHKI | HRSSPDNDLA | TVSALRNNGV | KLTPHNKETV |

|  70 | 80 | 90 | 100 | 110 | 120 |
|---|---|---|---|---|---|
| QRSDVLFLAV | KPHIIPFILD | EIGASIEDRH | IVVSCAAGVT | ISSIEKKLSA | FRFAPKVIRC |

|  130 | 140 | 150 | 160 | 170 | 180 |
|---|---|---|---|---|---|
| HINTFVVVRS | GATVIATGTH | AQVEDGRLMS | QLLSSVGFCT | SVSEDLIDAV | TGLSGSGPAY |

|  190 | 200 | 210 | 220 | 230 | 240 |
|---|---|---|---|---|---|
| AFTALDALAD | GGVKNGLPRR | LAVRLGAQAL | LGAARRLLHS | KQHPQQLKDN | VSSFGGATIS |

|  250 | 260 | 270 | 280 | 290 | 300 |
|---|---|---|---|---|---|
| ALNVLESGGF | RSLLINAVEA | SCIRTRSLQS | MADQEQVSPA | AIKKTILDKV | KLDSPRGTRL |

| 310 |
|---|
| SFSGHTELLF RRLAFRGRD |

SEQUENCE LISTING

```
<160> NUMBER OF SEQ ID NOS: 4

<210> SEQ ID NO 1
<211> LENGTH: 25
<212> TYPE: DNA
<213> ORGANISM: artificial
<220> FEATURE:
<223> OTHER INFORMATION: Morpholino antisense oligomer for Xenopus
      Pycr1

<400> SEQUENCE: 1
agctcctatg aagcccacac tcatg                                            25

<210> SEQ ID NO 2
<211> LENGTH: 25
<212> TYPE: DNA
<213> ORGANISM: artificial
<220> FEATURE:
<223> OTHER INFORMATION: Morpholino for zebrafish Pycr1

<400> SEQUENCE: 2
cagctccgat aaatcccaca ctcat                                            25
```

```
<210> SEQ ID NO 3
<211> LENGTH: 25
<212> TYPE: DNA
<213> ORGANISM: artificial
<220> FEATURE:
<223> OTHER INFORMATION: Morpholino for zebrafish Pycr2

<400> SEQUENCE: 3
ccgctccaat gaagcccaca ctcat                                              25

<210> SEQ ID NO 4
<211> LENGTH: 319
<212> TYPE: PRT
<213> ORGANISM: human

<400> SEQUENCE: 4
```

Met Ser Val Gly Phe Ile Gly Ala Gly Gln Leu Ala Phe Ala Leu Ala
1               5                   10                  15

Lys Gly Phe Thr Ala Ala Gly Val Leu Ala Ala His Lys Ile Met Ala
            20                  25                  30

Ser Ser Pro Asp Met Asp Leu Ala Thr Val Ser Ala Leu Arg Lys Met
        35                  40                  45

Gly Val Lys Leu Thr Pro His Asn Lys Glu Thr Val Gln His Ser Asp
    50                  55                  60

Val Leu Phe Leu Ala Val Lys Pro His Ile Ile Pro Phe Ile Leu Asp
65                  70                  75                  80

Glu Ile Gly Ala Asp Ile Glu Asp Arg His Ile Val Val Ser Cys Ala
                85                  90                  95

Ala Gly Val Thr Ile Ser Ser Ile Glu Lys Lys Leu Ser Ala Phe Arg
            100                 105                 110

Pro Ala Pro Arg Val Ile Arg Cys Met Thr Asn Thr Pro Val Val Val
        115                 120                 125

Arg Glu Gly Ala Thr Val Tyr Ala Thr Gly Thr His Ala Gln Val Glu
    130                 135                 140

Asp Gly Arg Leu Met Glu Gln Leu Leu Ser Ser Val Gly Phe Cys Thr
145                 150                 155                 160

Glu Val Glu Glu Asp Leu Ile Asp Ala Val Thr Gly Leu Ser Gly Ser
                165                 170                 175

Gly Pro Ala Tyr Ala Phe Thr Ala Leu Asp Ala Leu Ala Asp Gly Gly
            180                 185                 190

Val Lys Met Gly Leu Pro Arg Arg Leu Ala Val Arg Leu Gly Ala Gln
        195                 200                 205

Ala Leu Leu Gly Ala Ala Lys Met Leu Leu His Ser Glu Gln His Pro
    210                 215                 220

Gly Gln Leu Lys Asp Asn Val Ser Ser Pro Gly Gly Ala Thr Ile His
225                 230                 235                 240

Ala Leu His Val Leu Glu Ser Gly Gly Phe Arg Ser Leu Leu Ile Asn
                245                 250                 255

Ala Val Glu Ala Ser Cys Ile Arg Thr Arg Glu Leu Gln Ser Met Ala
            260                 265                 270

Asp Gln Glu Gln Val Ser Pro Ala Ala Ile Lys Lys Thr Ile Leu Asp
        275                 280                 285

-continued

```
Lys Val Lys Leu Asp Ser Pro Ala Gly Thr Ala Leu Ser Pro Ser Gly
    290                 295                 300

His Thr Lys Leu Leu Pro Arg Ser Leu Ala Pro Ala Gly Lys Asp
305                 310                 315
```

MUTEINS OF THE PYRROLINE-5-CARBOXYLATE REDUCTASE 1

CROSS-REFERENCE TO RELATED APPLICATIONS

This patent application is a continuation of U.S. patent application Ser. No. 13/322,750, filed Nov. 28, 2011, now abandoned, which is a U.S. National Phase Application under 35 U.S.C. 371 of International Application No. PCT/IB2010/001239, filed May 26, 2010, entitled MUTEINS OF THE PYRROLINE-5-CARBOXYLATE REDUCTASE 1, which claims the benefit of priority of U.S. provisional application No. 61/180,937, filed May 26, 2009, the content of which was hereby incorporated by reference in its entirety for all purposes.

INCORPORATION BY REFERENCE

This patent application incorporates by reference the material (i.e., Sequence Listings) in the ASCII text file named P46072_ST25.txt, created on Dec. 22, 2014 (modified Feb. 9, 2012), having a file size of 3,636 bytes.

FIELD OF THE INVENTION

The present invention relates to muteins of the pyrroline-5-carboxylate reductase 1 (PYCR1). The present invention also relates to a method of determining in a subject a predisposition of having an age related disorder associated with PYCR1, methods of identifying a compound capable of modifying the expression of PYCR1, and methods of treating a subject having an age-related disorder associated with PYCR1. The present invention further relates to a genetically modified animal and a method of modifying the expression of the PYCR1 gene in an animal.

BACKGROUND OF THE INVENTION

Wrinkly skin and bone loss are typical features associated with ageing. In some monogenetic diseases, these changes occur prematurely resulting in a progeroid appearance of affected individuals. As a clinical feature wrinkly skin or cutis laxa is used as a common denominator of several overlapping syndromal disorders including autosomal dominant cutis laxa (ADCL; MIM 123700), autosomal recessive cutis laxa type I (ARCL1; MIM 219100), autosomal recessive cutis laxa type II (ARCL2; MIM 219200, also called wrinkly skin syndrome (WSS; MIM 278250)), de Barsy syndrome (DBS; MIM 219150), and gerodermia osteodysplastica (GO, MIM 231070). Diagnosis is often difficult in these conditions due to a broad clinical overlap.

SUMMARY OF THE INVENTION

In a first aspect, the invention provides a mutein of the PYCR1, wherein at least one of the amino acid residues at sequence positions 4 to 220 and 222 to 266 of the wild type amino acid sequence of PYCR1 as set forth in Swiss-Prot Accession No. P32322 is mutated.

In a second aspect, the invention provides a mutein of PYCR1. The mutein includes a mutation of at least one of the amino acid residues at sequence positions 4 to 266 of the wild type amino acid sequence of PYCR1 as set forth in Swiss-Prot Accession No. P32322, wherein the mutation leads to a reduced function or loss of function of the mutein compared to the wild-type protein.

In a third aspect, the invention provides a nucleic acid molecule. The nucleic acid molecule includes a nucleotide sequence encoding a mutein as described above.

In a fourth aspect, the invention provides a method of determining in a subject a predisposition of having an age-related disorder associated with pyrroline-5-carboxylate reductase 1 (PYCR1). The method includes analyzing a nucleic acid sample obtained from a subject for the presence of a nucleotide sequence encoding a mutein as describe above, wherein the presence of the nucleotide sequence indicates a predisposition of the subject having or being at risk for having the age-related disorder.

In a fifth aspect, the invention provides use of a nucleic acid molecule comprising a nucleotide sequence encoding a mutein described above, for diagnosing or determining a predisposition of having an age-related disorder associated with PYCR1.

In a sixth aspect, the invention provides a method for identifying a compound capable of modifying the expression of a PYCR1 gene. The method includes: contacting a compound of interest with a nucleic acid molecule comprising a nucleotide sequence encoding pyrroline-5-carboxylate reductase 1 (PYCR1) or a functional fragment or mutant thereof, and measuring the expression of the nucleotide sequence encoding pyrroline-5-carboxylate reductase 1 (PYCR1) or a functional fragment or functional mutant thereof.

In a seventh aspect, the invention provides a method of modifying the expression of a PYCR1 gene in a cell. The method includes introducing a nucleic acid molecule comprising a nucleotide sequence encoding pyrroline-5-carboxylate reductase 1 (PYCR1) or a functional fragment or functional mutant thereof into the cell.

In an eighth aspect, the invention provides a method of treating a subject having an age-related disorder associated with PYCR1 or being at risk to develop an age-related disorder associated with PYCR1. The method includes introducing a nucleic acid molecule comprising a nucleotide sequence encoding pyrroline-5-carboxylate reductase 1 (PYCR1) or a functional fragment or functional mutant thereof into the subject.

In a ninth aspect, the invention provides a method of treating a subject having an age-related disorder associated with PYCR1 or being at risk to develop an age-related disorder associated with PYCR1. The method includes administering to the subject a compound capable of modifying the expression of a PYCR1 gene.

In a tenth aspect, the invention provides a genetically modified animal. The genetically modified animal includes a nucleic acid encoding pyrroline-5-carboxylate reductase 1 (PYCR1), wherein the nucleic acid is inactive.

In an eleventh aspect, the invention provides a method of modifying the expression of the PYCR1 gene in an animal. The method includes administering to the animal a compound capable of modifying the expression of the PYCR1 gene.

In a twelfth aspect, the invention provides a method of identifying a compound capable of modifying the expression of a PYCR1 gene. The method includes administering the compound of interest to a genetically modified animal as described above; and determining whether the compound is capable of modifying the expression of the PYCR gene.

In a thirteenth aspect, the invention provides a method of identifying a compound capable of modifying the expression of a PYCR1 gene. The method includes providing an isolated skin flap comprising at least one layer of living animal skin, said flap being attached to a test animal; and applying the compound of interest in contact with the living animal skin.

BRIEF DESCRIPTION OF THE DRAWINGS

Figure 1A:
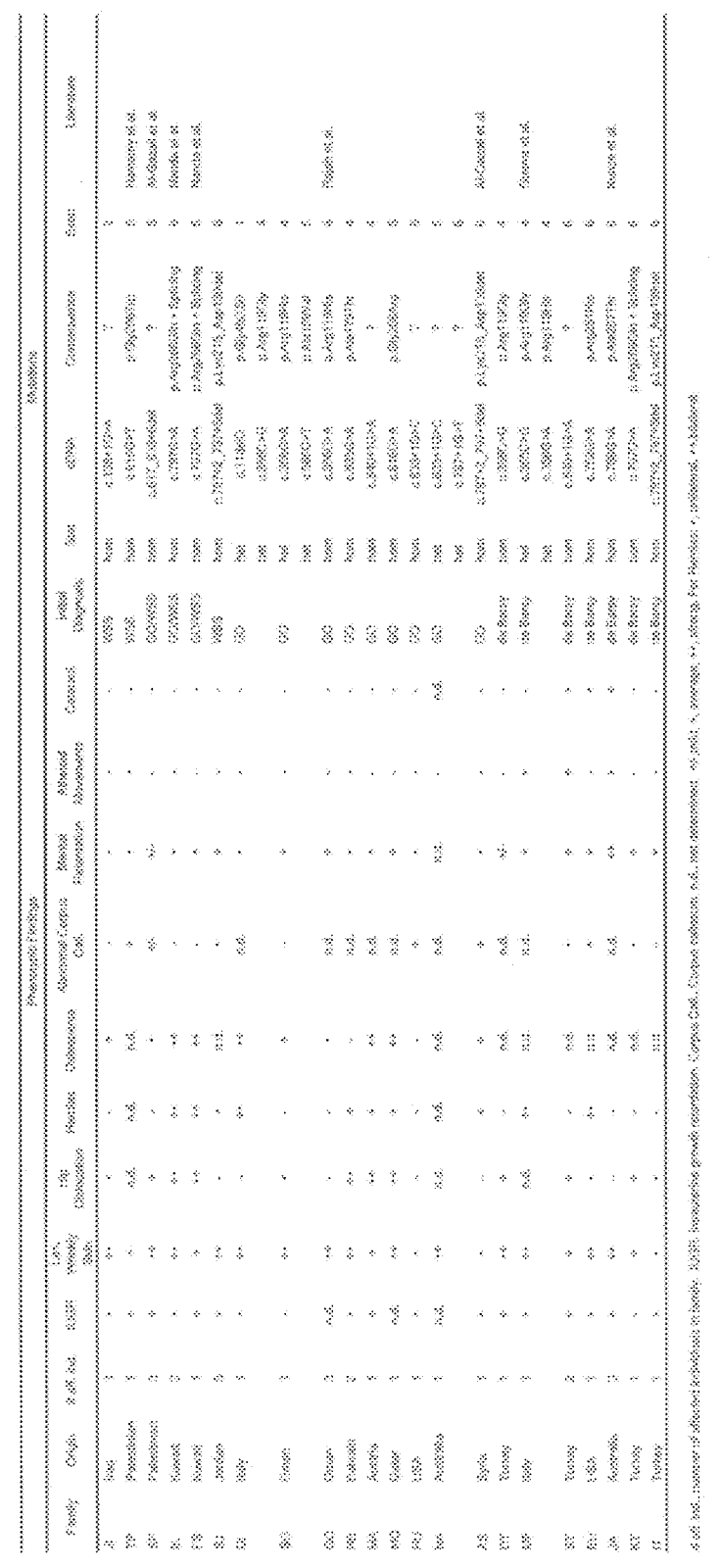

FIG. 1A sets forth phenotypic findings and mutations.

FIG. 12 shows the amino acid sequence of PYCR1 gene.

DETAILED DESCRIPTION OF THE INVENTION

Figure 1B:
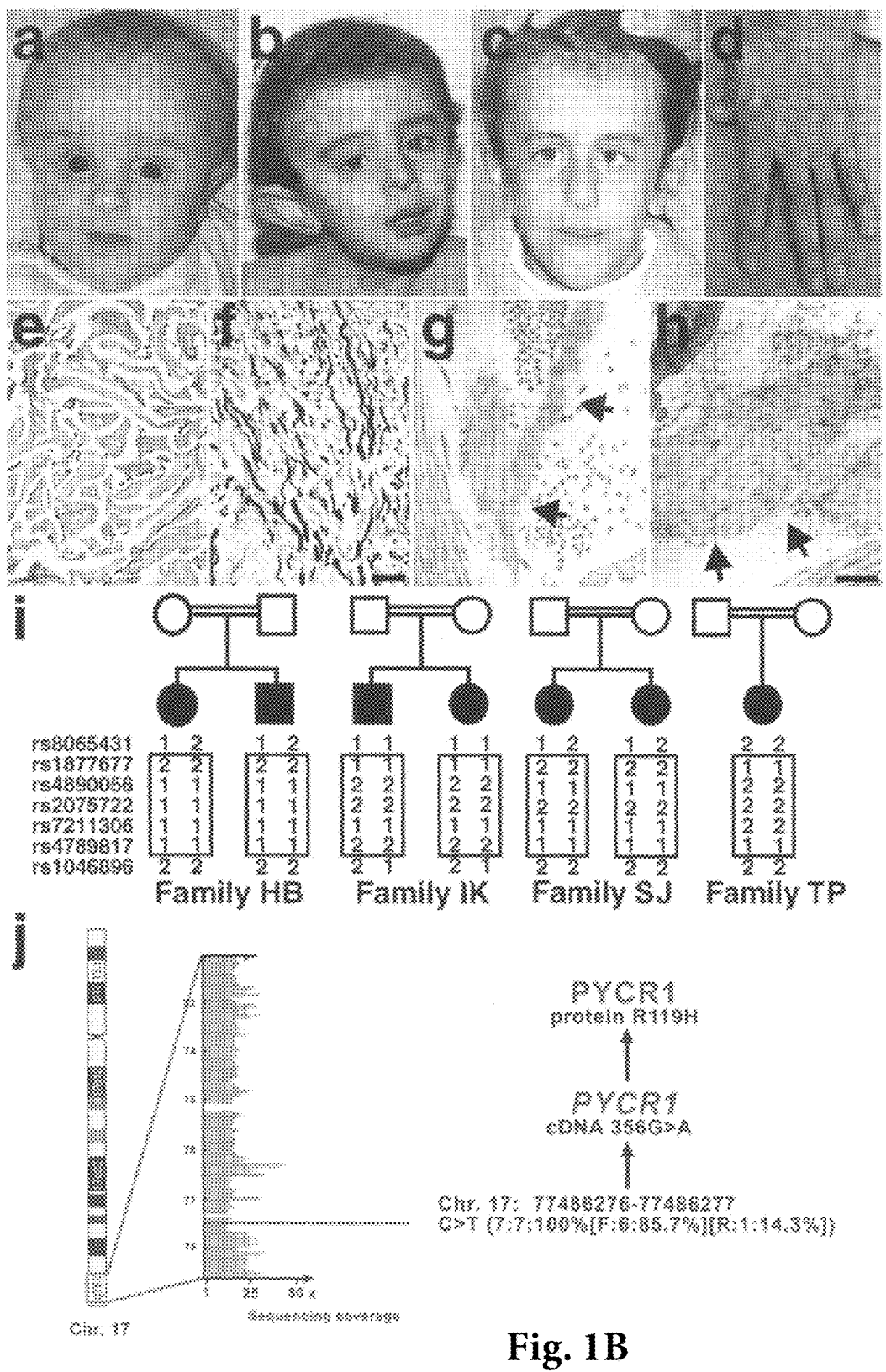
FIG. 1B illustrates phenotypic characteristics of patients with PYCR1-related autosomal recessive progeroid syndrome of de Barsy; findings in skin biopsy; homozygosity mapping; and genomic capture followed by next generation sequencing.

Mutations in PYCR1 associated with a spectrum of disorders characterized by wrinkly skin, osteoporosis and progeroid appearance are described herein. In this context, the inventors have detected disease-causing mutations in the PYCR1 gene. Such mutations of the PYCR1 gene are muteins of PYCR1, wherein at least one of the amino acid residues at sequence positions 4 to 220 and 222 to 266 of the wild type amino acid sequence of PYCR1 as set forth in Swiss-Prot Accession No. P32322 is mutated (see FIG. 6). In some embodiments, the muteins can comprise a mutation of at least one of the amino acid residues at sequence positions 4 to 266 of the wild type amino acid sequence of PYCR1 as set forth in Swiss-Prot Accession No. P32322, wherein the mutation leads to a reduced function or loss of function of the mutein compared to the wild-type protein.

The muteins described according to the invention can be identified or determined by any standard methods for example by homozygosity mapping using pooled DNA samples obtained from members of large kindreds in order to identify a chromosomal locus of interest or a candidate region thereof. Once a candidate region of the chromosomal locus is identified, the region can be screened for disease-causing mutations using conventional sequencing and genomic locus capture followed by high-throughput sequencing methods.

In some embodiments, a mutein described according to the present invention can also be derived from a single nucleotide polymorphism (SNP). The term "SNP" refers to a single nucleotide polymorphism at a particular position in the human genome that varies among a population of individuals. This single nucleotide polymorphism can for example be a single base change in the DNA sequence, with a usual alternative of two possible nucleotides at a given position. As used herein, a SNP may be identified by its name or by location within a particular sequence. Various methods known to persons skilled in the art can be used to produce SNPs. SNPs according to the present invention can for example be derived from comparison of sequence data from Expression Sequence Tag (EST) production projects, in particular if the libraries used were constructed using tissues from different individuals (Picoult-Newberg L., et al, Mining SNPs from EST databases, *Genome Res.* 9 (1999) 167-174). SNPs according to the present invention can also be derived using a reduced representation shotgun (RRS) approach as described in Altshuler D. et al., An SNP map of human genome generated by reduced representation shotgun sequencing, *Nature* 407 (2000) 513-516.

It is also possible to introduce mutations into the wild type amino acid sequence of PYCR1 as long as the desired purpose is achieved, for example to achieve a reduced or loss of function of a mutein of the invention compared to the respective wild-type protein. These mutations can for example include substitutions, deletions and insertions of the wild type amino acid sequence of PYCR1. Examples of possible alterations include conservatively modified variations where the alteration is the substitution of an amino acid with a chemically similar amino acid. Tables providing functionally similar amino acids are well known in the art. Examples of conservative substitutions are substitutions between: 1) alanine, serine, theronine; 2) aspartic acid and glutamic acid; 3) asparagine and glutamine; 4) arginine and lysine; 5) isoleucine, leucine, methionine, valine; and 6) phenylalanine, tyrosine, tryptophan. In other embodiments, the amino acid sequence of PYCR1 can also be modified by non-conservative alterations.

In certain embodiments, at least one of the amino acid residues at sequence positions 4, 119, 179, 189, 206, 251, 257 and 266 of the wild type amino acid sequence of PYCR1 is mutated. In this context, the mutation of the amino acid residue at sequence position 4 of the wild type amino acid sequence of PYCR1 can be mutated by a frameshift mutation leading to a translation stop codon occurring at the codon that encodes for sequence position 50 of the wild type amino acid sequence of PYCR1.

In other embodiments, the amino acid residue at sequence position 119 of the wild type amino acid sequence of PYCR1 can be replaced by glycine or histidine.

In some embodiments, the amino acid residue at sequence position 179 of the wild type amino acid sequence of PYCR1 can be replaced by a hydrophilic amino acid. The hydrophilic amino acid can for example be a hydroxyl-containing amino acid. Examples of such hydroxyl-containing amino acids include serine or threonine.

In some embodiments, the amino acid residue at sequence position 189 of the wild type amino acid sequence of PYCR1 can be replaced by a hydrophobic amino acid. The hydrophobic amino acid can for example be an aliphatic amino acid. Examples of such an aliphatic amino acid can include isoleucine, leucine and valine.

In some embodiments, the amino acid residue at sequence position 206 of the wild type amino acid sequence of PYCR1 can be replaced by an aromatic amino acid or a positively charged amino acid. Examples of the aromatic amino acid can include phenylalanine, tyrosine and tryptophan. Examples of the positively charged amino acid can include arginine or lysine.

In some embodiments, the amino acid residue at sequence position 251 of the wild type amino acid sequence of PYCR1 can be replaced by histidine. In other embodiments, the amino acid residue at sequence position 257 of the wild type amino acid sequence of PYCR1 can be replaced by a hydrophilic amino acid. This hydrophilic amino acid can for example be a hydroxyl-containing amino acid. Examples of such a hydroxyl-containing amino acid can be a serine or threonine.

In some embodiments, the amino acid residue at sequence position 266 of the wild type amino acid sequence of PYCR1 can be replaced by glutamine or asparagine.

The sequence of a mutein according to the present invention can also be modified for the purpose of improved stability, production, purification or applicability. For example, peptide segments which are not crucial for folding into a functional three-dimensional structure can be removed for these purposes, if wanted. Disulfide bonds can be eliminated by substitution of the cysteine residues or new disulfide bonds can be introduced at another site. Optionally, cysteine residues can also be newly introduced in order to prepare, for example, corresponding protein conjugates by chemical coupling with other components. Binding sites for further ligands, such as for example metal ions, can also be built into the mutein.

The term "amino acid residue" as used herein refers to an amino acid either in the D or L form or to an amino acid mimetic that can be incorporated into a polypeptide by an amide bond. Accordingly, the positively charged amino acid residue at position 89 can for example either be a naturally occurring amino acid residue that is positively charged under physiological conditions such as arginine or lysine or a non-natural mimetic such as a lysine residue the α-amino group of which is alkylated in order to yield a (quarternary) ammonium-salt having a permanent positive charge.

The term "wild type" in reference to an animal or an amino acid sequence as used herein, means a phenotype, genotype or a gene that predominates in a natural population of organisms or strain of organisms in contrast to the forms that were genetically altered in a natural or artificial environment.

In an illustrative embodiment of the invention, the clinical features of 35 affected individuals from 22 families were studied and summarized in Table 1. These features include congenital skin wrinkling, most pronounced on the dorsum of hands and feet, generalized connective tissue weakness, finger contractures, hernias, osteoporosis and a triangular face with a progeroid appearance which is due to lax skin and hypoplasia of the jaw often resulting in prognathism (FIG. 1B*a-d*). Ultrastructural investigation of the skin revealed rarefaction and fragmentation of elastic fibers similar to changes described in autosomal recessive cutis laxa (ARCL) (FIG. 1B*e-h*). No glycosylation abnormalities were detected by standard diagnostics. A variable degree of mental retardation was observed in all cases but one. In a substantial number of patients, agenesis of the corpus callosum was evident. While most affected individuals were classified as gerodermia osteodysplastica (GO) or wrinkly skin syndrome (WSS), more severely affected individuals also showed childhood cataracts or dystonic movements and were therefore diagnosed as de Barsy syndrome (DBS) (Al-Gazali, L. I., et al., Gerodermia osteodysplastica and wrinkly skin syndrome: are they the same? *Am J Med Genet* 101, 213-20 (2001); Hamamy, H., et al., Wrinkly skin syndrome. *Clin Exp Dermatol* 30, 590-2 (2005); Nanda, A. et al. Gerodermia osteodysplastica/wrinkly skin syndrome: report of three patients and brief review of the literature. *Pediatr Dermatol* 25, 66-71 (2008); and Kunze, J. et al. De Barsy syndrome—an autosomal recessive, progeroid syndrome. *Eur J Pediatr* 144, 348-54 (1985)).

Homozygosity mapping in five consanguineous families revealed a minimal candidate region of 2.8 Mb on chromosome 17q25 between markers rs8065431 and rs1046896 (FIG. 1*i*). With the exception of P4HB, which was excluded by sequencing, none of the 59 genes in this region was an obvious candidate. Therefore, conventional sequencing and genomic loci capture were combined followed by high throughput sequencing (FIG. 1*j*). The latter identified 552 genomic mismatches, of which 8 were novel SNPs, which causes non-synonymous mutations (FIG. 1A). The inventors have so identified muteins of PYCR1, the gene encoding for pyrroline-5-carboxylate reductase 1 enzyme (PYCR1).

In another aspect of the invention, there is provided a nucleic acid molecule comprising a nucleotide sequence encoding a mutein according to the present invention. The term "nucleic acid" as used herein refers to any nucleic acid molecule in any possible configuration, such as a linearized single stranded, a double stranded or a combination thereof. Examples of such nucleic acids may include, but are not limited to DNA molecules (e.g., cDNA or genomic DNA), RNA molecules (e.g., mRNA), antisense RNA, short interfering (siRNA), micro RNA (miRNA), analogues of the DNA or RNA generated using nucleotide analogues or using nucleic acid chemistry, cDNA synthetic DNA, a copolymer of DNA and RNA, oligonucleotides, PNA (protein nucleic acids), or combinations thereof. DNA or RNA may be of genomic or synthetic origin and may be single or double stranded. A respective nucleic acid may furthermore contain non-natural nucleotide analogues and/or be linked to an affinity tag or a label.

The term "nucleotide" includes native (naturally occurring) nucleotides, which include a nitrogenous base selected from the group consisting of adenine, thymidine, cytosine, guanine and uracil, a sugar selected from the group of ribose, arabinose, xylose, and pyranose, and deoxyribose (the combination of the base and sugar generally referred to as a "nucleoside"), and one to three phosphate groups, and which can form phosphodiester internucleosidyl linkages. The "nucleotide" also refers to nucleotide analogs. Such analogs can have a sugar analog, a base analog and/or an internucleosidyl linkage analog. Additionally, analogs exhibiting non-standard base pairing are also included (see for example U.S. Pat. No. 5,432,272). Such nucleotide analogs include nucleotides that are chemically modified in the natural base ("base analogs"), chemically modified in the natural sugar ("sugar analogs"), and/or chemically modified in the natural phosphodiester or any other internucleosidyl linkage ("internucleosidyl linkage analogs"). In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases, e.g., adenine, guanine, cytosine, uracil, and thymine, and analogs of the naturally occurring nucleotide bases, e.g., 7-deazaadenine, 7-deazaguanine, 7-deaza-8-azaguanine, 7-deaza-8-azaadenine, N6δ2-isopentenyladenine, N2-dimethylguanine (dmG), 7-methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2thiopyrimidine, 6-thioguanine, 4-thiothymine, 4-thiouracil, O.sup.6-methylguanine, N.sup.6-methyladenine, O.sup.4-methylthymine, 5,6-dihydrothymine, 5,6-dihydrouracil, pyrazolo[3,4-D]pyrimidines (see for example U.S. Pat. Nos. 6,143,877 and 6,127,121), ethenoadenine, indoles such as nitroindole and 4-methylindole, and pyrroles such as nitropyrrole.

The term "complementary" is intended to mean the relationship of the nucleotides/bases on two different strands of DNA or RNA, where the bases are paired (guanine with cytidine, adenine with thymine (DNA) or uracil (RNA)).

In certain embodiments, a nucleic acid molecule used according to the invention can comprise a nucleotide sequence encoding a mutein of the present invention. In other embodiments, the nucleic acid used according to the invention can comprise a nucleotide sequence pyrroline-5-carboxylate reductase 1 (PYCR1) or a functional fragment or mutant thereof. The term "functional mutant" of PYCR1 used herein refers to a variant protein other than the muteins of the present invention, in which the function is essentially retained. For example, one or more amino acids that is not relevant for said function may have been exchanged. The term "functional fragment" as used herein refers to a fragment of PYCR1, having sufficient length to provide its desired function.

In this context, a nucleic acid molecule as used herein such as DNA can for example be regarded to be "capable of expressing a nucleic acid molecule or a coding nucleotide sequence" or capable "to allow expression of a nucleotide sequence" if it contains regulatory nucleotide sequences which contain transcriptional and translational information and such sequences are "operably linked" to nucleotide sequences which encode a mutein of the present invention. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of the synthesis. Such regions will normally include non-coding regions which are located 5' and 3' to the nucleotide sequence to be expressed and which are involved with initiation of transcription and translation such as the TATA box, capping sequence, CAAT sequences.

The nucleic acid molecule of or used in according to the invention can in some embodiments be altered by inserting or deleting at least one nucleotide from the nucleotide sequence. In other embodiments, at least one of the splice sites of the nucleotide sequence of the nucleic acid molecule can be mutated. The term "splice site" refers to specific nucleic acid sequences that are capable of being recognized by the splicing machinery of a eukaryotic cell as suitable for being cut and/or ligated to a corresponding splice site. Splice sites allow for the excision of introns present in a pre-mRNA transcript. Typically the 5' portion of the intron is referred to as the donor splice site and the 3' corresponding splice site is referred to as the acceptor splice site. The term splice site includes, for example, naturally occurring splice sites, engineered splice sites. Engineered splice sites may be mutated sites for example. The mutation of the splice sites enables the control of the ratio between the polypeptides translated from the different populations of transcripts. Splice sites are well known in the art and any may be utilized in the present invention.

In some embodiments, the nucleic acid molecule may be comprised in a vector, for example an expression vector. Such a vector is capable of integrating the nucleic acid as described above and can comprise a sequence coding for restriction cleavage site which adjoins the nucleic acid encoding the mutein of the present invention or PYCR1 or a functional fragment or mutant thereof in 5' or/and 3' direction. The vector can also contain replication sites and control sequence derived from a species compatible with the host that is used for expression. In this context, the term "vector" relates to a single or double-stranded circular nucleic acid molecule that can be introduced, e.g. transfected into cells and replicated within or independently of a cell genome. A circular double-stranded nucleic acid molecule can be cut and thereby linearised upon treatment with restriction enzymes. An assortment of nucleic acid vectors, restriction enzymes, and the knowledge of the nucleotide sequences cut by restriction enzymes are readily available to those skilled in the art.

A nucleic acid molecule encoding a mutein of the present invention or PYCR1 or a functional fragment or mutant thereof can be inserted into a vector by cutting the vector with restriction enzymes and ligating the two pieces together. Any vectors suitable for genetic cloning that are known to the person skilled in art can be used in the present invention. Examples of these vectors may include but are not limited to pUC18, pUC19, BR322, pBR325, pBR327 and pBR328. The nucleic acid encoding the mutein of the invention or PYCR1 or a functional fragment or mutant thereof and/or the respective vector may be contained within a host cell capable of expressing the nucleic acid. The host cell disclosed herein can also contain a nucleic acid as defined above. The host cell as used herein includes any host cells that can be used as expression systems to produce recombinant proteins in particular the mutein as described above or PYCR or a functional fragment or mutant thereof. Exemplary host cells are prokaryotic host cells, such as, but are not limited to, *Escherichia coli* (*E. coli*), *Bacillus subtilis*, and *Salmonella typhimurium*; and eukaroyotic host cells including mammalian, avian, fungal, and insect cells. Various methods of introducing the vector into the host cell are known to persons skilled in the art, such as transformation, transfection, electroporation and biolistics.

The invention also provides a nucleic acid molecule comprising a nucleotide sequence encoding a mutein of the invention for use in diagnosing or determining a predisposition of having an age-related disorder associated with PYCR1. The age-related disorder can be but is not limited to cutis laxa (wrinkly skin syndrome), de Barsy syndrome and gerodermia osteodysplasia.

In a further aspect, the invention provides a method of determining in a subject a predisposition of having an age-related disorder associated with pyrroline-5-carboxylate reductase 1 (PYCR1). The method includes analyzing a nucleic acid sample obtained from the subject for the presence of a nucleotide sequence encoding a mutein of the invention, wherein the presence of the nucleotide sequence indicates a predisposition of the subject having or being at risk for having the age-related disorder.

The invention also provides a method of identifying a compound capable of modifying the expression of a PYCR1 gene. The method includes contacting a compound of interest with a nucleic acid molecule comprising a nucleotide sequence encoding PYCR1 or a functional fragment or mutant thereof. The method further includes measuring the expression of the nucleotide sequence encoding PYCR1 or a functional fragment or functional mutant thereof. Subsequently, the result of the measurement can be compared with that of a control measurement in which the compound of interest is not added.

The invention also provides a genetically modified animal. The genetically modified animal includes a nucleic acid encoding PYCR1 gene in which the nucleic acid is inactive. In some embodiments, the nucleic acid leads to a loss of function of the PYCR1 gene. The nucleic acid that encodes the PYCR1 gene can be inactivated by genetic methods that are well known in the art. The nucleic acid can for example be inactivated by using gene knockout or knockdown methods, morpholino antisense oligomers, or other known methods that can lead to a loss of function of the PYCR1 gene. The term "animal" can include all vertebrate, including humans. It can also include an individual animal in all stages of development, including embryonic and foetal stages. To obtain a genetically modified animal according to the present invention, the genetic material of the animal can be modified using genetic engineering techniques such as recombinant DNA technology. Recombinant DNA can for example be produced through the addition of a relevant DNA into an existing organismal genome, such as a plasmid, to code for or alter different traits for a specific purpose. Examples of such an animal can include but are not limited to a *xenopus*, a fish, an amphibian, a reptile and a bird. The genetically modified animal used in the present invention may also be a mammal. In some embodiments, the mammal may include a human, a rodent, *Canis*, Ungulate, Felidae, Leporidae, and Macaque. Examples of a rodent include, but are not limited to, a mouse, rat, squirrel, chipmunk, gopher, porcupine, beaver, hamster, gerbil, guinea pig, chinchilla, prairie dog, and groundhog. Examples of *Canis* include, but are not limited to a dog, wolf, coyote and jackal. Examples of Ungulate include, but are not limited to a horse, donkey, zebra, sheep, pig, goat, camel, giraffe and moose. Examples of Felidae include, but are not limited to a cat, caracal, cougar, cheetah and leopard. Examples of Leporidae include, but are not limited to a rabbit, hare and jackrabbit. An example of a Macaque includes a rhesus monkey.

In another aspect, the invention provides a method of identifying a compound capable of modifying the expression of a PYCR1 gene. The method includes administering the compound of interest to an animal or a genetically modified animal as described herein. The method further includes determining whether the compound is capable of modifying the expression of the PYCR1 gene.

A compound of interest used in according to the present invention can be formulated into any form as long as the compound is capable of modifying the expression of the PYCR1 gene. The compound can for example be formulated in a form of a pharmaceutical or cosmetic composition. Examples of a cosmetic composition includes gels, ointment, cream, lotion, serum, pastes, soaps, aerosols, soluble tablets, powder, sticks, water-based or oil-based suspensions and emulsions.

In this context, the expression of the PYCR1 can be modified either at the gene or protein level. A gene expression level or an amount of a protein level is deemed to be "modified" or "modulated" when the gene expression/activity/amount of the respective protein is increased or decreased by for example about 10%, about 25%, about 50%, about 75%, about 100%, or higher, as compared to the control level. Alternatively, an expression level or an activity level or a protein level/amount is deemed "increased" or "decreased" when gene expression/or an activity/protein level is increased or decreased by for example at least about 0.1, at least about 0.2, at least about 1, at least about 2, at least about 5, or at least about 10 or more fold as compared to a control level. Thus, in some embodiments, the compound of interest used in the methods of the invention can for example increase or decrease the expression of the PYCR1 gene.

It is thus a further aspect of the invention to provide a method of modifying the expression of a PYCR1 gene in a cell. The method includes introducing a nucleic acid molecule comprising a nucleotide sequence encoding pyrroline-5-carboxylate reductase 1 (PYCR1) or a functional fragment or functional mutant thereof into the cell. Any cell may be used in the present method of the invention. In some embodiments, the cell is obtained or derived from a host organism, which may be any organism. The cell may be directly taken, e.g. isolated, from a respective host organism in form of a sample such as e.g. a biopsy or a blood sample. It may also have been obtained, e.g. isolated, from a host organism and subsequently been cultured, grown, transformed or exposed to a selected treatment. In some embodiments, the cell used according to the invention may be comprised in a host organism. It may for instance be present in the blood or in tissue, including in an organ, of the host organism. The host organism from which the cell is derived or obtained, including isolated, purified or enriched, or in which it is included, may be any organism such as a microorganism, an animal, such as a fish, an amphibian, a reptile, a bird, a mammal, including a rodent species, an invertebrate species, e.g. of the subclass Lissamphibia that includes e.g. frogs, toads, salamanders or newts, or a plant. Examples of mammals include, but are not limited to, a rat, a mouse, a rabbit, a squirrel, a vole, a platypus, a chicken, a cow, a goat, a sheep, a pig, a dog, a mouflon, a guinea pig, a hamster, a chimpanzee, a rhesus monkey a macque or a human.

The invention also provides a method of modifying the expression of the PYCR1 gene in an animal including the animals described above. The method includes administering to the animal a compound capable of modifying the expression of the PYCR1 gene. The compound can in some embodiments include a nucleic acid molecule that is capable of modifying the expression of the PYCR1 gene. Examples of such a nucleic acid molecule are described above and include an antisense RNA, short interfering (siRNA), micro RNA (miRNA), peptide nucleic acid (PNA) and combinations thereof.

It is another aspect of the invention to provide a method of treating a subject having an age-related disorder associated with PYCR1 or being at risk to develop an age-related disorder associated with PYCR1. In some embodiments, the method includes introducing a nucleic acid molecule comprising a nucleotide sequence encoding PYCR1 or a functional fragment or functional mutant thereof into the subject. In other embodiments, the method can also include administering a compound capable of modifying the expression of the PYCR1 gene. A respective use may for example be the manufacture of a medicament or a pharmaceutical composition for this purpose. Accordingly, the method of the invention includes the use of a nucleic acid or a compound as defined above, including the use in the manufacture of a medicament. The compound that is capable of modifying the expression of PYCR1 can be identified using the methods of the invention described herein. In this context, the methods of or used according to the invention can be performed in vivo or in vitro.

The term "administer" relates to a method of incorporating a compound of interest, a nucleic acid according to the invention or a respective pharmaceutical composition thereof, into one or more cells or tissues of an organism. Exemplary routes of administration of a respective compound, nucleic acid or pharmaceutical composition thereof include oral, transdermal, and parenteral delivery. Suitable routes of administration may for example include depot, oral, rectal, transmucosal, intravenous, intramedullary injections, as well as intrathecal, direct intraventricular, intraperitoneal, intranasal or intraocular injections.

Figure 2:
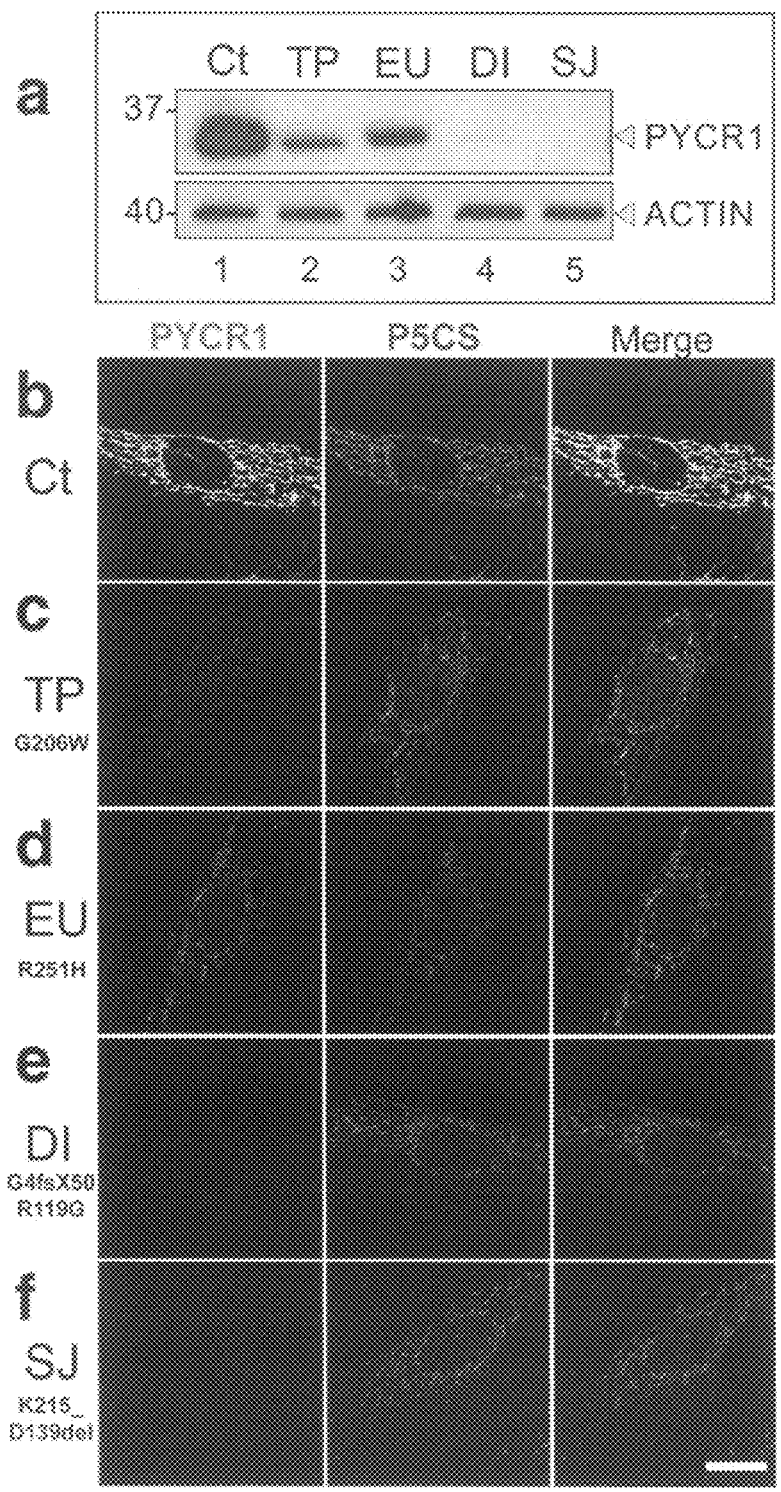
FIG. 2 illustrates the effect of PYCR1 mutations.
Figure 6:
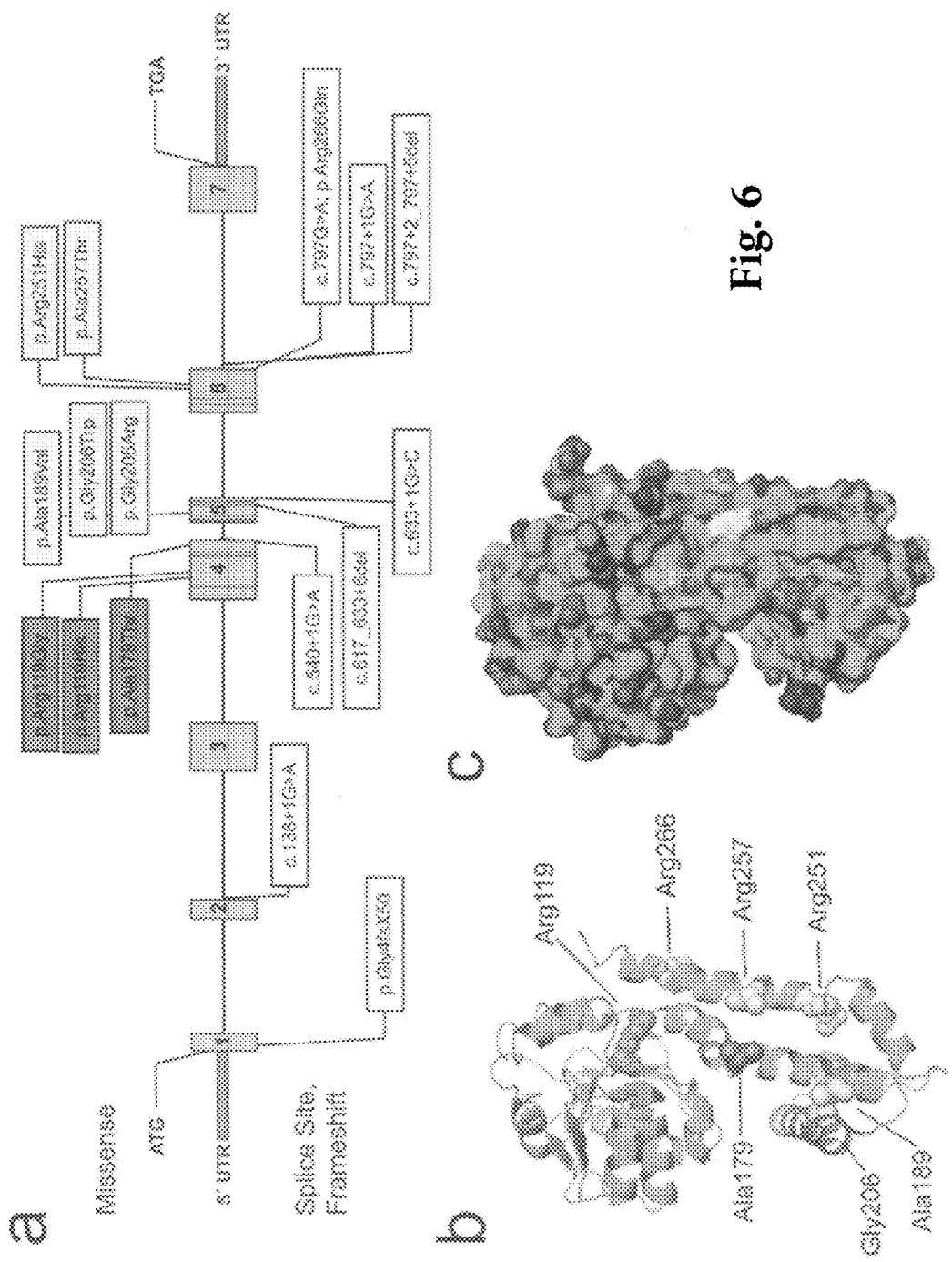
FIG. 6 illustrates localisation of mutated PYCR1 residues.

In an illustrative embodiment, eight missense mutations, one frameshift mutation, five splice site mutation and one 22 bp deletion comprising the exon-intron boundary of exon 5 were identified (FIG. 1A, FIG. 6). Five of these mutations were recurrent, even though the affected individuals did not have a common ethnic background. To examine PYCR1 protein expression, skin fibroblasts were isolated from probands and their unaffected siblings (FIG. 2). Strongly reduced PYCR1 protein levels were detected in fibroblasts from patient (SJ) with a homozygous splice site mutation and a compound heterozygous patient (DI) with a missense and a frame shift mutation (FIG. 2a). The missense mutations p.Gly206Trp and p.Arg251 His resulted in a reduction of protein levels relative to control cells (FIG. 2a). The PYCR1 protein, which has been often described as cytosolic, co-localized with the mitochondrial matrix protein A-Pyrroline-5-carboxylate synthase (P5CS), which also belongs to the proline metabolic pathway (FIGS. 2b-f). It can therefore be concluded that PYCR1 is a mitochondrial protein and that the mutations described herein lead to a loss-of-function.

In another illustrative embodiment, Pycr1 expression analysis in mouse tissues showed highest mRNA levels in bone and skin, two tissues most severely affected (FIG. 7b). Two paralogues of PYCR1 exist in human, the highly similar PYCR2 and the more distantly related PYCRL. No significant expression changes in fibroblasts from individuals with PYCR1 mutations were observed for PYCR2 or P5CS (FIG. 7a). As PYCR1 catalyzes the obligatory and final step in de novo proline synthesis, the question of whether the affected individuals exhibit hypoprolinemia was investigated. Serum proline levels in affected individuals were slightly reduced, but within normal range (FIG. 8a). Likewise, cultured skin fibroblasts did not show evidence for reduced proline levels (FIG. 8b) or for reduced proliferation rates in medium without proline (FIG. 8c), arguing against a proline auxotrophy.

In a further illustrative embodiment, the mitochondrial network was examined in more detail, based on mitochondrial localization of PYCR1. Ultrastructural analysis revealed abnormal morphology of mitochondria and their cristae (FIGS. 3a,b). These differences were exacerbated upon oxidative stress (FIGS. 3c-e). Addition of $H_2O_2$ to the cell culture media induced the collapse of the filamentous mitochondrial network in cells from affected individuals, while almost no changes were observed in mitochondria of control cells (FIG. 3f). Under normal culture conditions patient and control fibroblasts showed no differences in their levels of apoptosis. However a 5-fold increase in cell death in patients' fibroblasts when compared to control was detected after a short exposure to $H_2O_2$ (FIG. 3f). This suggests that PYCR1 is involved in the cell's response to oxidative stress.

Figure 9:
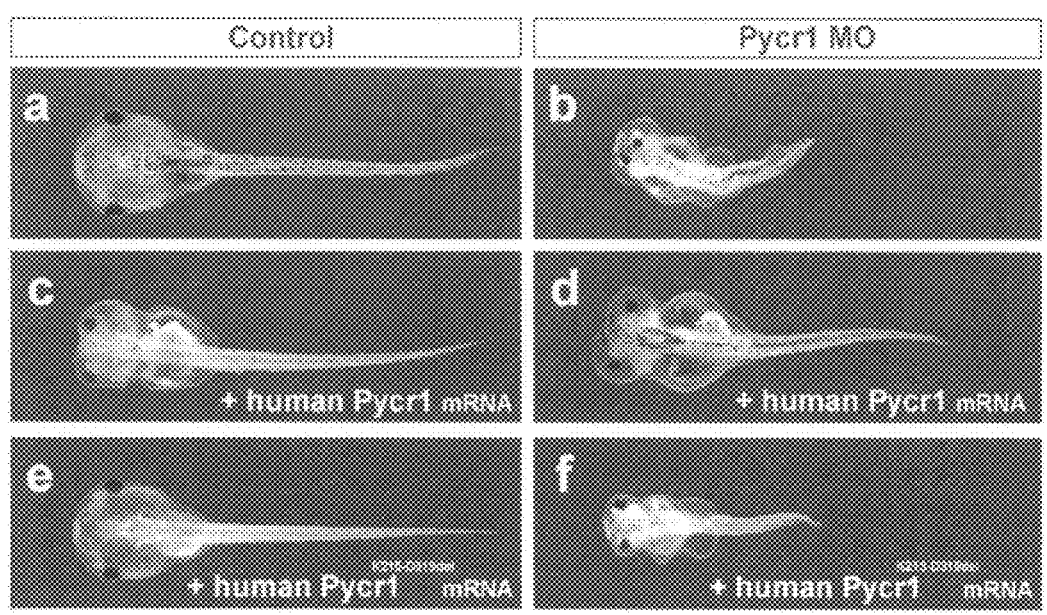
FIG. 9 illustrates tadpoles showing partial rescue of the Pycr1 morphant phenotype by overexpression of human wild-type Pycr1 mRNA but not mutant Pycr1 K215-D319del mRNA.

In another illustrative embodiment, the function of PYCR1 during embryogenesis was investigated, since patients with mutations in PYCR1 are affected at birth. Conserved throughout evolution, PYCR1 orthologues are found across bacteria, plants, insects and vertebrates (FIG. 4a). To model the disease in Xenopus embryos, a morpholino (MO) against Pycr1 according to the invention was designed (FIG. 4b). Pycr1-depleted embryos showed no obvious developmental defects until early tadpole stage. By stage 30, Pycr1 morphant embryos failed to develop eyes and a tail bud (FIG. 4c,d). This phenotype was shown to be cell-autonomous, as injection only in ventral or dorsal blastomeres prevented development of the eyes and the tail, respectively (FIG. 4e-i). Skin alterations became apparent and later developed into ectodermal edemas at the swimming tadpole stage (FIG. 4j,i). Histological skin sections revealed disorganization of the epithelium with enlarged cells and nuclei (FIG. 4k,m). Microinjection of human PYCR1 mRNA partially rescued the phenotype observed in Pycr1 morphants while human PYCR1 mRNA mimicking the K215-D319Ddel mutation was without effect (FIG. 9). Likewise, morpholino-mediated knockdown of Pycr1 and Pycr2 in zebrafish led to a similar skin phenotype (FIG. 11a,b) which was rescued by injection of human wild-type PYCR1 mRNA (FIG. 11d, e). Pycr1 morphants had no visible circulating red blood cells (FIG. 10a,b). This anemia was traced back to the loss of Scl expression, a marker for primitive hematopoiesis, at stage 25 (FIG. 5e,f).

By stages 25-30, skin hypoplasia was accompanied by a significant increase in the number of apoptotic cells (FIG. 5a-d, g). As the skin defects observed in Pycr1 morphants might be caused by anemia, a parabiosis was performed between wild-type and Pycr1 MO-injected embryos (FIG. 10c). There was a decrease in the extent of ectodermal edemas with shared blood circulation but skin hypoplasia, apoptosis and stunted growth were not rescued in Pycr1 morphants following parabiosis (FIG. 5g-i). It can be concluded that Pycr1 plays independent roles during blood formation and skin development in Xenopus. The anemia observed in frogs may reflect the dual roles played by Pycr1 in this species, which lacks the Pycr2 gene. In humans, PYCR2's role in erythrocytes has been well documented[24,25]. Taken together the above results suggest that loss-of-function mutations in PYCR1 compromise mitochondrial function which leads to apoptosis during embryogenesis and to a general inability to thrive during adult life.

PYCR1 belongs to the NAD(P)-binding Rossmann-fold domains superfamily that catalyzes the conversion of 1-pyrroline-5-carboxylate (P5C) to L-proline. Several heritable disorders have been linked to the proline metabolic pathway[10]. Most notably, mutations in P5CS cause a condition of mental retardation, joint hypermobility, and skin laxity (OMIM 612652)[11-13]. As in the patients described herein, P5CS-deficiency is not consistently characterized by reduced serum proline levels[11,12] Furthermore, fibroblasts from these patients did not exhibit the proliferation defect described for P5CS-deficiency[13]. The phenotype of PYCR1-related disease overlaps with other forms of cutis laxa, mirrored by the fact that affected individuals from this cohort have been previously described under the diagnoses WSS, GO, or DBS[5,6,8,9,14,15]. While GO does not lead to intellectual impairment, ARCL2 often includes mild or moderate mental retardation and brain anomalies[16]. Mutations in ATP6V0A2, encoding subunit a2 of the V-ATPase complex that localizes to endosomes and the Golgi apparatus, have been identified in ARCL2[4]. Mutations in another vesicular Golgi protein, GORAB, were identified in GO. The phenotypic similarities suggest a common, yet to be determined, pathogenetic mechanism in these conditions. Interestingly, increased apoptosis is also seen in fibroblasts from ARCL2 patients with ATP6V0A2 defects[17].

The generation of potentially harmful reactive oxygen species (ROS) in aerobic metabolism has become a central focus of ageing research[18]. ROS were initially regarded as toxic side products of oxidative phosphorylation, but more recently their importance for redox-dependent signalling processes has emerged[18,19]. Indeed, proline has been implicated in the regulation of ROS levels[20,21]. Furthermore, PYCR1 and -2 have been implicated in the regulation of the NAD(P)H/NAD(P)$^+$ ratio in the cytoplasm and in the mitochondrion[22]. Mitochondrial fragmentation has been described to impair cellular function in neurodegenerative disorders[23]. Furthermore, changes in mitochondrial fusion can trigger senescence[24]. Although the exact role of PYCR1 for mitochondrial function and integrity remains to be determined, the fact that its orthologues in other species such as *Saccharomyces*, *Arabidopsis* and *Drosophila* have been linked to stress resistance suggests that also human PYCR1 may provide adaptive protection against stress by maintaining a reservoir of rapidly mobilizable proline and reducing equivalents into mitochondria.

In summary, mutations in PYCR1 leading to a loss of PYCR1 function are a major cause of autosomal recessive cutis laxa evoking a phenotype that overlaps with gerodermia osteodysplastica, ARCL type 2 and ARCL type 3. The pathophysiological basis is an impaired mitochondrial function leading to developmental defects through increased apoptosis. The importance of mitochondrial function in the process of ageing highlighted by the inventors can help to develop novel treatment strategies for common age-related disorders[27]. Such treatment strategies may include new pharmaceutical or cosmetic applications to treat age-related disorders or prevent the effects of ageing, such as skin wrinkling. As an illustrative example, screening assays using an experimental animal can be generated to screen for new cosmetic compounds or pharmaceutical compositions. An example of the experimental animal may include a nude mouse in which a living human skin graft carrying a mutation of the PYCR1 gene is grafted onto the nude mouse.

In one aspect, the invention also provides a method of identifying a compound capable of modifying the expression of a PYCR1 gene. The method includes providing an isolated skin flap comprising at least one layer of living animal skin, said flap being attached to a test animal, as for example described in U.S. Pat. No. 4,677,968. The method further includes applying the compound of interest to the living animal skin.

In this context, to screen for compounds that are capable of modifying the expression of a PYCR1 gene, the compound of interest can be directly applied onto the living human skin which is grafted onto the nude mouse. The compounds that are used according to this method can be of any form including a pharmaceutical or cosmetic composition as described above.

In some embodiments, the skin flap can include cells that express the mutein of the invention. The cells can for example include fibroblast cells. The skin flap can include a layer of living human skin on one surface and a living animal skin on the other surface. The skin flap can be served by an isolated vasculature which can be attached to the test animal. The living animal skin can be of the same or different species than the test animal. The animal can be a human or a rodent, including an athymic rodent for example.

In summary, the above screening assay may provide a method for identifying and analyzing the effect of cosmetic or pharmaceutical compositions in contact with the living human skin. The compound of interest can be tested on the skin by direct surface application. The behaviour and effect of the living human skin in response to different compounds can be studied.

EXAMPLES

The following non limiting examples are also illustrative of the process described above and are not to be construed as limiting the scope of the present invention.

Genotyping and Linkage Analysis.

DNA samples were obtained from 22 families after participants gave their informed consent and after approval by the local ethic commission (Ethikkommission der Charite). We performed genome-wide linkage analysis in eight families using the Affymetrix GeneChip® Human Mapping 250K Arrays (Affymetrix, Santa Clara, Calif.). Genotypes were called by the GeneChip® DNA Analysis Software (GDAS v2.0, Affymetrix). We verified sample genders by counting heterozygous SNPs on the X chromosome. Relationship errors were evaluated with the help of the program Graphical Relationship Representation. The program PedCheck was applied to detect Mendelian errors and data for SNPs with such errors were removed from the data set. Non-Mendelian errors were identified by using the program MERLIN and unlikely genotypes for related samples were deleted[28]. Nonparametric linkage analysis using all genotypes of a chromosome simultaneously was carried out with MERLIN. Parametric linkage analysis was performed by a modified version of the program GENEHUNTER 2.1 through stepwise use of a sliding window with sets of 110 or 200 SNPs. Haplotypes were reconstructed with GENEHUNTER 2.1 and presented graphically with HaploPainter[29].

Mutation Analysis.

Positional candidate genes were obtained from the GenBank (http://www.ncbi.nlm.nih.gov/mapview/) and Ensembl (http://www.ensembl.org) databases. Genes were analyzed by direct sequencing of DNA with primers flanking each exon. Primer sequences were based on the reference sequences of each gene. The primer sequences for PYCR1 mutation screening are given in supplementary Table 1. Sequence analysis was done with the BigDye Terminator cycle sequencing kit (Applied Biosystems, Foster City, Calif.), and products were run on a 3730 DNA Analyzer (Applied Biosystems, Foster City, Calif.).

Genomic loci capture. Briefly, custom arrays (Agilent 244K) were designed to target every exonic sequence of the genes present in the locus 17q25 between 72,048,357 and 78,774,742 excluding the highly repeated regions. DNA libraries were prepared following the Illumina library generation protocol version 2.3 and were hybridized to the custom arrays according to the Agilent CGH 244K array protocol, then washed, eluted and amplified. Each sample was submitted to one channel of Illumina flowcell and sequenced by Illumina Genome Analyzer (GA) using standard manufacturer's protocol. The image data was processed by the provided GA Pipeline version 1.0 and all sequences were aligned to the human reference genome (UCSC build 18, http://genome.ucsc.edu) by Blat-like Fast Accurate Search Tool (BFAST, https://secure.genome.ucla.edu/index.php/BFAST, N. Homer et al., in preparation). Mismatches were filtered for those seen 2 or more times, where the mutation was seen 100% of the time (homozygous), and did not overlap with a known dbSNP129 entry mismatch. The open source SeqWare project which provides a LIMS tool for tracking samples (SeqWare LIMS) and a pipeline for sequence analysis (SeqWare Pipeline), (http://segware.sourceforge.net) was used throughout this work.

Cell Culture.

Human skin fibroblasts were cultivated in DMEM (Lonza) supplemented with 10% foetal calf serum (FCS) (Lonza), 1% Ultraglutamine (Lonza) and 1% penecillin/streptomycine (Lonza) at 5% $CO_2$ and 37° C.

Quantitative PCR.

RNA was isolated from organs of P4 mice using the Trizol (Invitrogen) method. 1 μg of RNA was reverse transcribed using the Revert Aid kit (Fermentas) and random hexamers. Quantitative PCR was performed with SYBR green (Applied Biosystems). Primers are given in supplementary FIG. 1.

Western Blot Analysis.

Mitochondrial and cytosolic fractions of whole cell lysates of primary skin fibroblasts were obtained with a mitochondria isolation kit for mammalian cells (Thermo Scientific) and resolved by electrophoresis in SDS polyacrylamide gels. For Western blot analysis PVDF membranes were probed with the antibodies: anti-Actin A5060 (Sigma) 1:1000, rabbit anti-PYCR1 (Proteintech) 1:500.

Immunofluorescence Analysis.

For immunofluorescence, cells were washed in phosphate-buffered saline (PBS) three times. Cells were fixed in 4% (wt/vol) paraformaldehyde in 1×PBS for 10 min and permeabilized with 0.4% (vol/vol) Triton-X100 in 3% BSA in 1×PBS for 10 min at 4° C. Specific antibodies against PYCR1 (rabbit anti-PYCR1 (Proteintech) 1:500 and P5CS (mouse anti P5CS (Abnova) 1:300 were incubated over night in 3% BSA at 4° C. For visualization an anti-mouse IgG Alexa Fluor 555 (Invitrogen, Molecular Probes) and an anti-rabbit IgG Alexa Fluor 488 (Invitrogen, Molecular Probes) conjugate was applied. DNA was stained by DAPI and cells were mounted in Fluoromount (Scientific Services). Images were collected by using an LSM 510 meta (Carl Zeiss, Gottingen, Germany) with a ×63 Plan Apochromat oil immersion objective.

Mitochondrial Morphology.

Morphology of the mitochondrial network was investigated after treatment with hydrogene peroxide (neoLab). Cells were cultivated up to 50% confluence. Treatment with every substance was performed in normal medium. Cells were loaded with 100 nM Mito Tracker Red CM-H2XRos (Invitrogen). Cells were incubated with 500 μM $H_2O_2$ for 5 min. Cells were fixed in 4% (wt/vol) paraformaldehyde in 1×PBS for 10 min at 4° C. DNA was stained by DAPI and cells were mounted in Fluoromount (Scientific Services). Pictures of every sample were collected randomly using a BX60 Olympus microscope and the mitochondrial morphology was determined.

Apoptosis Assay.

For apoptosis measurement after hydrogene peroxide (neoLab) treatment cells were incubated with 200 μM $H_2O_2$ for one hour without FCS. After stress periode medium was changed to normal medium with 0.4% FCS and cells were incubated at normal conditions for additionally 24 hours. The same experiment was performed with medium supplemented with 5 mM L-Proline (Sigma-Adrich). Cells were fixed in 4% (wt/vol) paraformaldehyde in 1×PBS for 10 min and permeabilized with 0.1% (vol/vol) Triton-X100 in 3% BSA in 1×PBS for 2 min on ice. For apoptosis determination the TUNEL assay (Roche) was performed according to manufacturer specifications. Cells were fixed in 4% (wt/vol) paraformaldehyde in 1×PBS for 10 min at 4° C. DNA was stained by DAPI and cells were mounted in Fluoromount (Scientific Services). Pictures were collected randomly. Each experiment was performed three times. More than 2000 cells were analysed per assay.

Proliferation Assay.

For the assessment of the proliferation rate $2.5 \times 10^4$ cells were seeded on glass coverslips. The cells were incubated for 8 hours in medium containing 10 μM Bromodesoxyuridine (BrdU) (Roche). Cells were fixed in 4% (wt/vol) paraformaldehyde in 1×PBS for 10 min after 24, 48 and 72 hours and then incubated in 3 N HCL for 10 min at room temperature. They were permeabilized with 0.1% (vol/vol) Triton-X100 in 3% BSA in 1×PBS for 30 min at 4° C. Specific antibody against BrdU (G3G4) 1:500 were incubated for 1 hour at room temperature. For visualization an anti-mouse IgG Alexa Fluor 488 (Invitrogen, Molecular Probes) conjugate was applied. DNA was stained by DAPI and cells were mounted in Fluoromount (Scientific Services). The experiment was also performed in medium with 10% dialysed FCS and in medium supplemented with 5 mM L-Proline (Sigma-Adrich).

Morpholino Oligos and RNA Injections.

The 25-bp Morpholino (MO) antisense oligomers for *Xenopus* Pycr1 was obtained from Gene Tools and consisted of the following sequence: 5'-AGCTCCTATGAAGCCCA-CACTCATG-3'. The MO was resuspended in sterile water to a concentration of 1 mM according to manufacturer's instructions. Embryos were injected four times radially at the two- to four-cell stage with 4 nl (33 ng MO/injection). Synthetic capped mRNAs of human PYCR1 cDNA was used for rescue experiments at 200 pg in each blastomere at the 4-cell stage. For zebrafish experiments MOs against zebrafish Pycr1 and zebrafish Pycr2 were obtained from Gene Tools: DrPycr1-MO 5'-CAGCTCCGATAAATCCA-CACTCAT-3' and DrPycr2-MO 5'-CCGCTCCAAT-GAAGCCCACACTCAT-3'. Embryos were injected at 1-cell stage with 4 nl (33 ng MO/injection) or 2 nl of each MO when co-injected. Rescue experiments were performed by co-injection of 20 pg or 200 pg human PYCR1 capped mRNA, which were in vitro transcribed with SP6-Kit (Ambion).

Embryological Methods.

Protocols for fertilization, injections, whole-mount in situ hybridization and TUNEL can be found at http:/www.reversade.com-a.googlepages.com/protocols[30]. Analysis of cell death on live embryos was performed by incubating tadpoles in the dark for 30 min with acridine orange (2 μg/ml) in Barth 0.1×. After extensive washes in Barth 0.1×, images of embryos were captured under fluorescence (480 nm) with a Leica DFC 300 FX camera. Parabiosis was performed at stage 22, on dechorionated embryos joined by ventral ectoderm after small incisions were performed. Parabiotic embryos were cultured in Barth 0.1× until healed and transferred into Steinberg 1× solution. A stereomicroscope M205 FA equipped with an ICD camera from Leica was used to capture images of embryos in successive focal planes. Images were then merged into one picture with Photoshop CS3®.

Generation of a Test Animal for Skin Grafting.

To obtain an isolated skin flap on a test animal, incisions were made along the three sides of a subject area of a nude mouse. Prior to the incision, the nude mouse was anesthetized by intraperitoneal ketamine. Human skin was obtained from the patients of the families referred to in Table 1 for grafting onto the nude mouse. The human skin graft was approximately the same size and configuration as the skin flap created on the nude mouse. The human skin graft were either used immediately or stored in RPMI-1640 with 10% bovine serum at 4° C. for up to approximately 72 hours or until used for grafting. To graft the human skin graft onto the nude mouse, the human skin graft was surgically attached to the subcutaneous surface of the isolated flap area of the nude mouse. The skin flap and the human skin graft was sutured in place, creating a sandwich having a vasculature sandwiched between the skin layers, such that substantially all blood leaving the flap flow through the isolated vasculature. Once the human skin and the affected skin area of the nude mouse have grown together to form an integral flap, the vascularised flap was then moved through a subcutaneous tunnel to the dorsal side of the mouse, where it was sutured in place for testing. To prevent rejection of the human skin graft, the mouse was provided with an injection of cyclosporine subcutaneously at a dosage of 25 mg/kg/day.

Accession Codes.

Genbank Refseq DNA: *Homo sapiens* PYCR1 isoformA NM_006907.2, *Homo sapiens* PYCR1 isoform B NM_153824.1, *Xenopus laevis* PYCR1 NM_001091619, *Danio rerio* PYCR1 BC095354; *Danio rerio* PYCR2 BC060905.

Illustrative Examples Describing the Invention

FIG. 1B Phenotypic characteristics of patients with PYCR1-related autosomal recessive progeroid syndrome of de Barsy. (a) Affected 9 month old girl from family DI with typical triangular face. (b) Similar facial appearance in a six year old affected boy from family DT. c) Seven year old affected girl from family TP initially diagnosed as wrinkly skin syndrome. Note typical facial gestalt including prognathism. (d) Skin wrinkling at the dorsum of the hand and typical adducted thumbs in an affected individual from family HB. (e-h) Findings in skin biopsy from affected individual from family DI. (e,f) Weigert staining reveals sparse, thinned and fragmented elastic fibers in the reticular dermis compared to control, scale bar 100 μm. (g,h) Ultrastructural analyses corroborate the markedly reduced elastic fiber (arrows) size with a reduction in both the fibrillar and amorphous components in an affected individual from family DI compared to control, scale bar 500 nm. (i) Homozygosity mapping resulted in a minimal candidate region of 2.8 Mb on chromosome 17q25 between markers rs8065431 and rs1046896. Only the four most informative pedigrees are shown. (j) Genomic capture followed by next generation sequencing of the maximal candidate region extending from 72.05-78.77 Mb. A cytosine to thymidine sequence change was sequenced seven times in a patient from family GO. This base change resulted in a single p.Arg119His mutation in the protein encoded by the PYCR1 gene.

FIG. 2 Effect of PYCR1 mutations. (a) Western blot analysis of PYCR1 protein expression in primary skin fibroblasts from controls and patients. ACTIN served as a loading control. Note absence of PYCR1 expression in affected individuals DI and SJ while EU and TP show a significant reduction. (b-f) Immunofluorescent detection of PYCR1 and P5CS in skin fibroblasts. (b) In control fibroblasts PYCR1 and the mitochondrial matrix protein P5CS co-localize. In fibroblasts from patients DI (e) and SJ (d) immunostaining for PYCR1 signals is undetectable. In contrast, in fibroblasts from TP (c) and EU (d) PYCR1-staining in mitochondria is reduced in intensity relative to control. Note abnormal mitochondrial network in DI, SJ and TP. Scale bar 20 μm.

Figure 3:
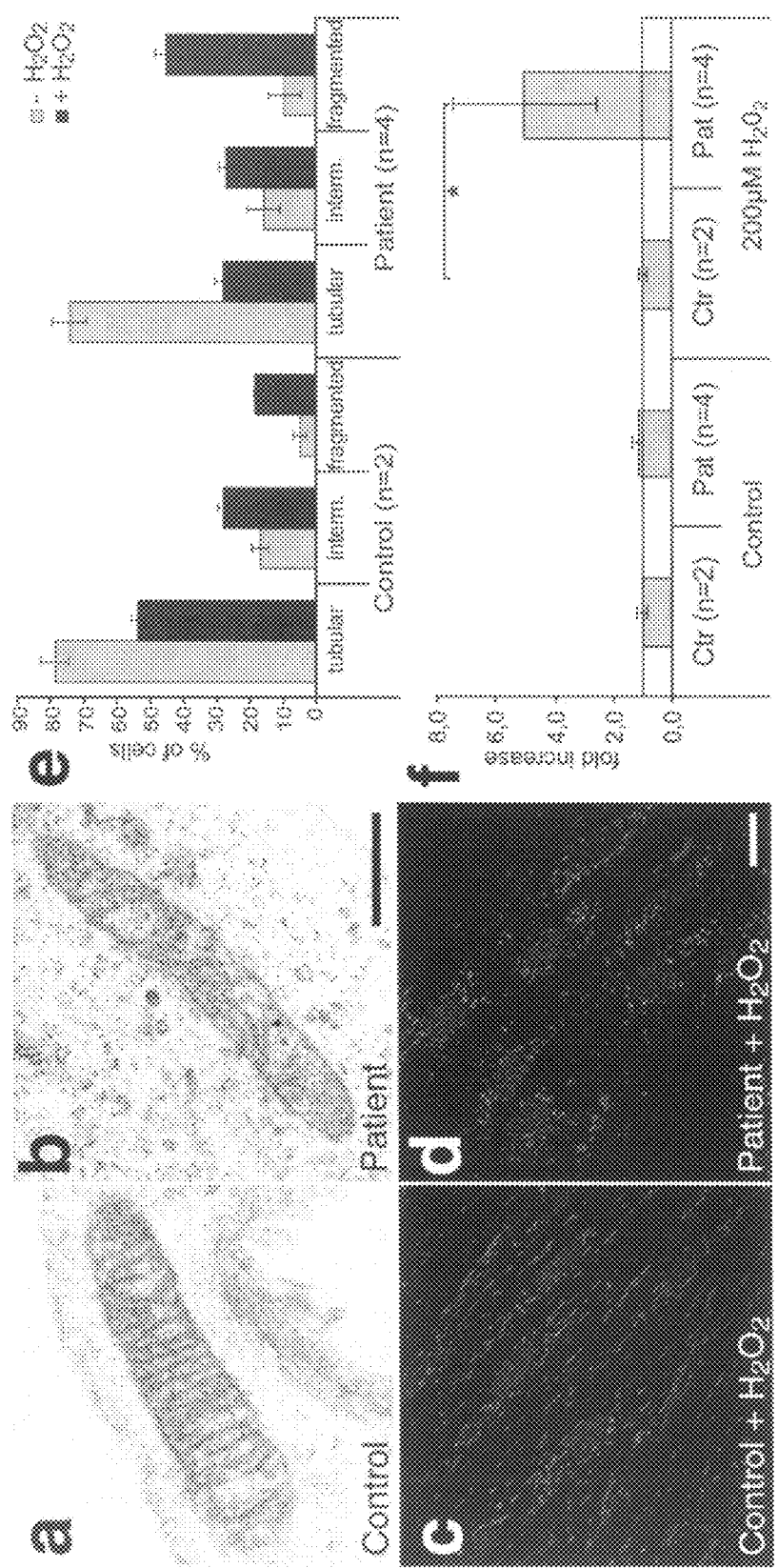
FIG. 3 illustrates mitochondrial morphology; quantification of mitochondrial morphology changes upon oxidative stress; and quantification of apoptotic cell death.

FIG. 3 Loss of PYCR1 causes increased sensitivity to oxidative stress. (a,b) Ultrastructural analysis of mitochondrial morphology. While mitochondria (a) in control fibroblasts have regularly arranged cristae, (b) fibroblasts from affected individual DI show strongly altered cristae and a reduced diameter, Scale bar: 1 μm. (c,d) Changes in mitochondrial morphology upon oxidative stress. Addition of 500 μM $H_2O_2$ to cell culture media for 10 min leads to mitochondrial network collapse in fibroblasts from affected individual from family SJ (d), tubular mitochondrial network remains largely intact in control cells (c), scale bar: 20 μm. (e) Quantification of the mitochondrial morphology changes upon oxidative stress. Without oxidative stress (grey bars) most control (n=2) and patient (n=4) cells exhibit tubular mitochondria. Only few cells with fragmented or intermediate (interm.) morphologies were seen. In contrast, under oxidative stress (black bars) the number of cells with fragmented mitochondria increased much more strongly in patient cells than in controls. Data from two independent experiments are averaged. (f) Quantification of apoptotic cell death by TUNEL 24 hours after oxidative stress. Fibroblasts from controls (n=2) and affected individuals (n=4) showed no differences in apoptosis rates under normal culture conditions (control). 24 hours after a 10 min incubation with 200 μM $H_2O_2$ a 5-fold increase (p=0.026) in apoptosis was observed in cells from affected individuals. Numbers are normalized to control cells in control experiment (n=1).

Figure 4:
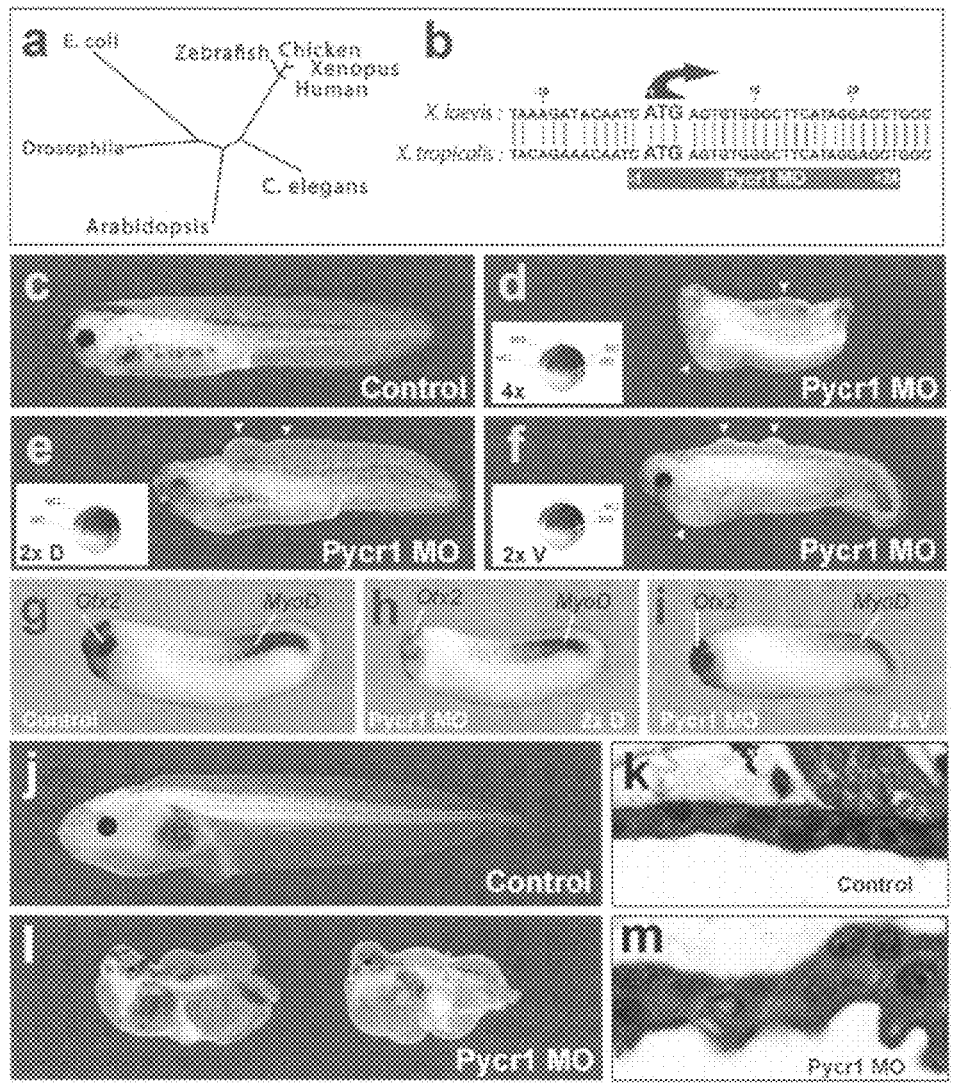
FIG. 4 illustrates Pycr1 evolution; design of a translation-blocking morpholino oligo for *Xenopus* Pycr1; phenotypes of Pycr1 *Xenopus* morphants; and skin sections.

FIG. 4 Phenotype of Pycr1 *Xenopus* morphants. (a) Pycr1 is evolutionary conserved from bacteria, plants, insects to vertebrates. (b) Design of a translation-blocking morpholino oligo for *Xenopus* Pycr1. (c) Control embryo at stage 30. (d) Pycr1 morphants injected in each blastomere at the 4-cell stage failed to grow a tail and had under-developed eyes. (e) Dorsal MO-injections impaired eye but not tail development. (f) Ventral MO-injections impaired tail but not eye development, suggesting that Pycr1 is required cell-autonomously. White arrowheads point to skin wrinkles which develop into ectodermal edemas by stage 40. (g) Stage 23 control tadpole stained with forebrain/midbrain marker Otx2 and somite marker MyoD. (h) Dorsal depletion of Pycr1 affects dorso-anterior structures marked by Otx2 but not ventro-posterior structures marked by MyoD. (i) Ventral depletion of Pycr1 affects ventro-posterior structures marked by MyoD but not dorso-anterior structures marked by Otx2. (j) Control embryo at the swimming tadpole stage. (l) Pycr1 MO-injected embryos suffered severe growth retardation and displayed large ectodermal edemas over the entire body. (k) Histological skin section of control embryo at stage 45 showed bi-layered epidermis consisting of outer periderm and inner sensorial layer. (m) Disorganized architecture of epidermis with enlarged cells, nuclei and cellular protrusions.

Figure 5:
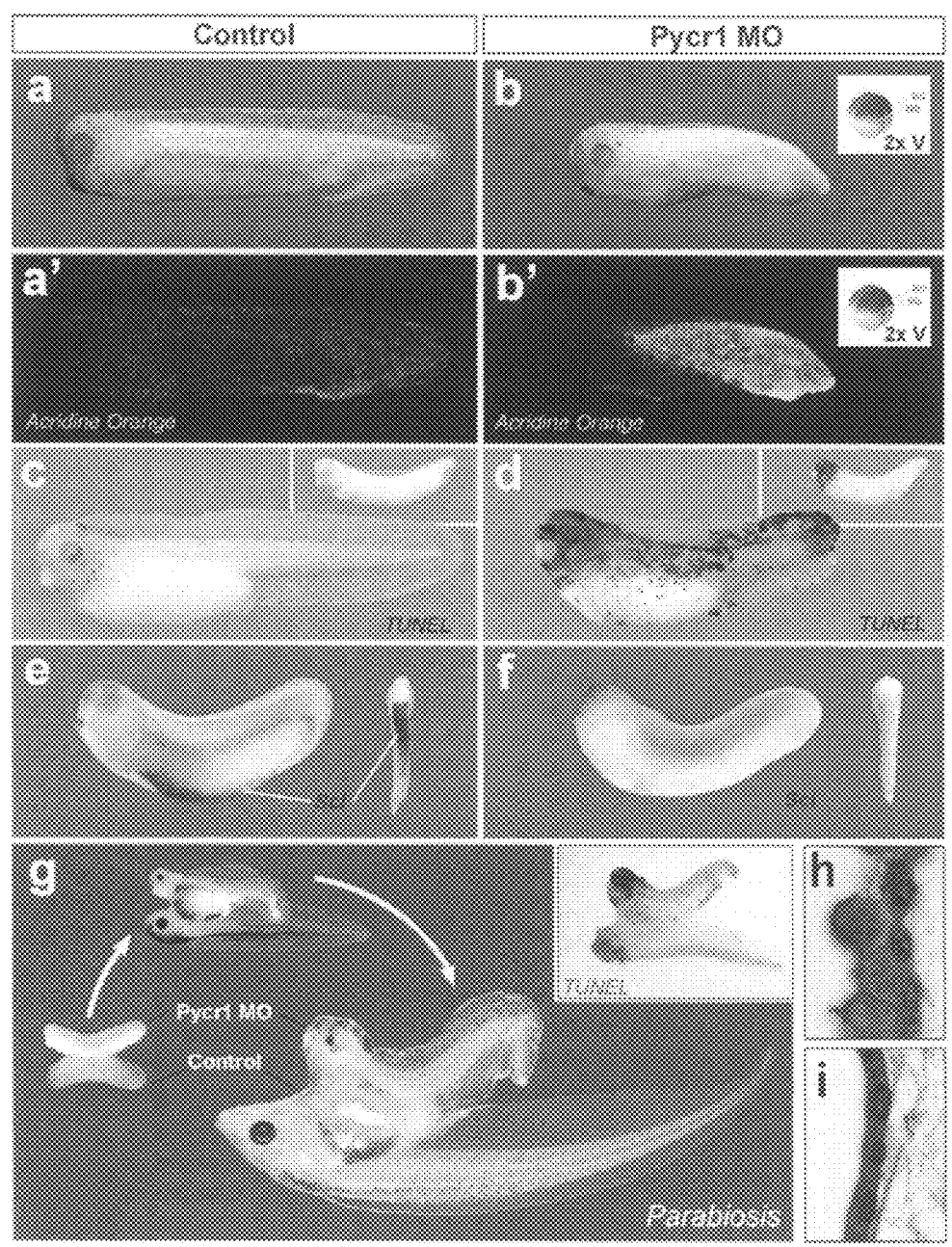
FIG. 5 illustrates a control embryo; Pycr1 morphants; parabiosis performed between a Pycr1-depleted tadpole and a control; an epidermis of a Pycr1 parabiotic morphant embryo; and epidermis of a parabiotic control tadpole.

FIG. 5 Skin hypoplasia in Pycr1 morphants is accompanied by spontaneous apoptosis and is independent of anemia. (a) Control embryo at stage 30. (a') Acridine orange background staining of embryo shown in (a). (b) Pycr1 morphant resulting from ventral MO injections only. (b') Acridine orange labeling of dying cells (intense green) in embryo shown in (b). Note that only the ventro-posterior half of the embryo, derived from the injected ventral blastomeres, is undergoing apoptosis. (c) TUNEL staining in stage 33 tadpole indicated few apoptotic cells (inset: control at stage 25). (d) Pycr1 morphants have a markedly increased number of dying cells at stage 33 relative to control (inset: stage 25). (e) Scl expression at stage 25 marks site of primitive hematopoiesis in ventral ectoderm of control embryo. (f) Scl expression was abrogated in Pycr1 morphants which suffered from anemia (Supplementary FIG. 5). (g) Parabiosis performed at stage 22 between a Pycr1-depleted tadpole (top) and control (bottom) failed to rescue apoptosis (inset: stage 33), stunted growth and skin defects despite shared blood circulation (Supplementary FIG. 5). (h) Histological staining showed that epidermis of Pycr1 parabiotic morphant embryo remained disorganized relative to control. (i) Histological section through epidermis of parabiotic control tadpole at stage 45 showing normal skin architecture.

FIG. 6 Localisation of mutated PYCR1 residues. a) Genomic localisation. Note that mutations accumulate in exons 4-6. Red=position of amino acids essential for substrate binding. b,c) Position of residues affected by missense mutations in 3D structure of the PYCR1 monomere (According to Meng et al.). b) Ribbon model. c) Surface model. Orange=residue 100% conserved; yellow=residue 80-100% conserved; white=splice site and frame shift mutations.

Figure 7:
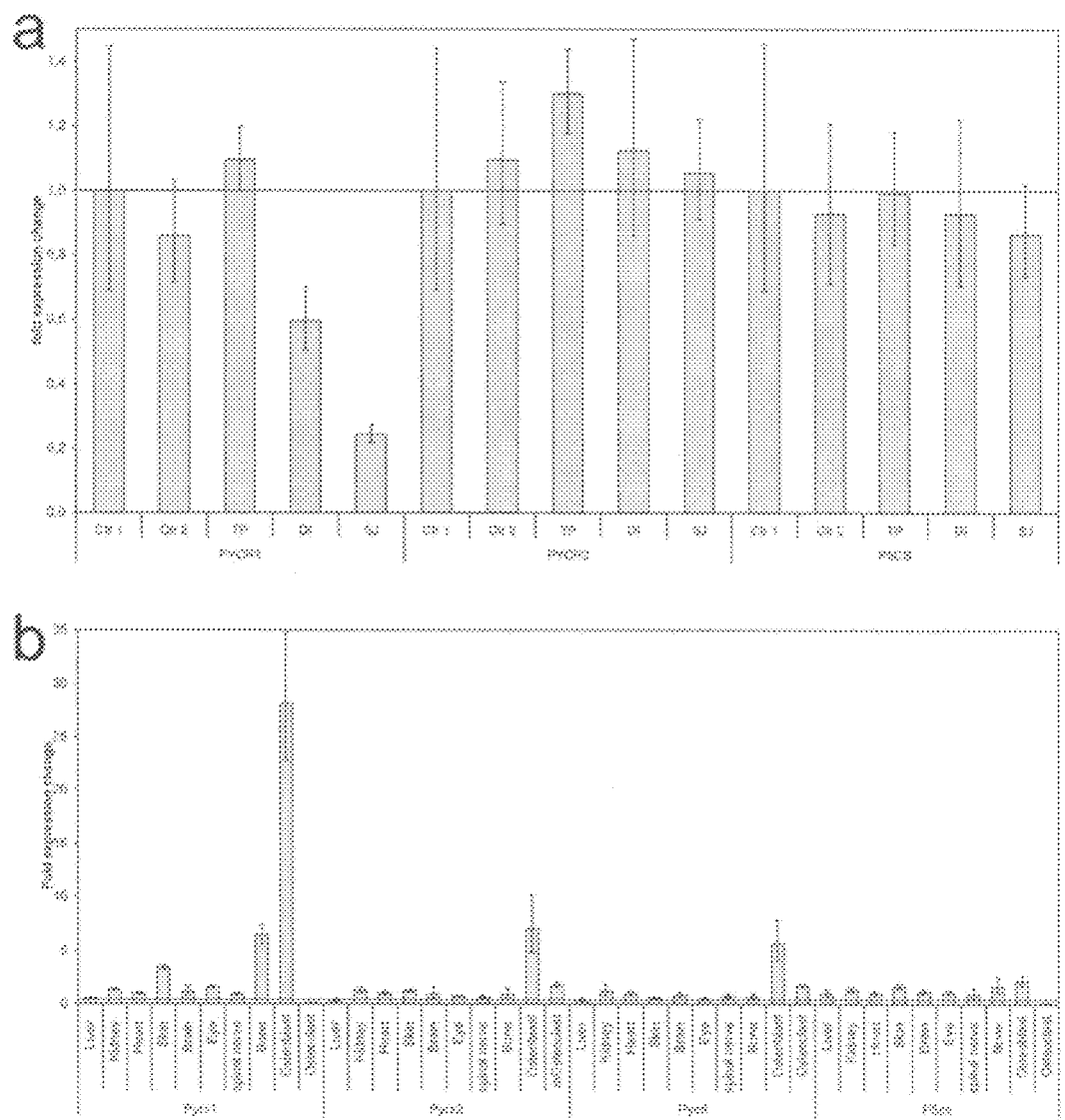
FIG. 7 illustrates gene expression changes in fibroblasts from individuals with PYCR1 mutations and controls; and expression of genes involved in proline metabolism in tissues.

FIG. 7 a) Gene expression changes in fibroblasts from individuals with PYCR1 mutations and controls determined by qualitative PCR. While the Gly206Trp mutation in patient TP does not affect PYCR1 expression levels the mutations in D1 and SJ clearly reduce mRNA levels due to nonsense-mediated decay. Expression of PYCR2 and P5CS is not affected. b) Expression of genes involved in proline metabolism in tissues from 4 day old mice normalized to expression levels in the heart determined by quantitative PCR. Note extremely high Pycr1 expression levels in osteoblasts and skin. Pycr2 and Pyrc1 are also most highly expressed in osteoblasts, but otherwise show uniform expression, as does P5cs.

Figure 8:
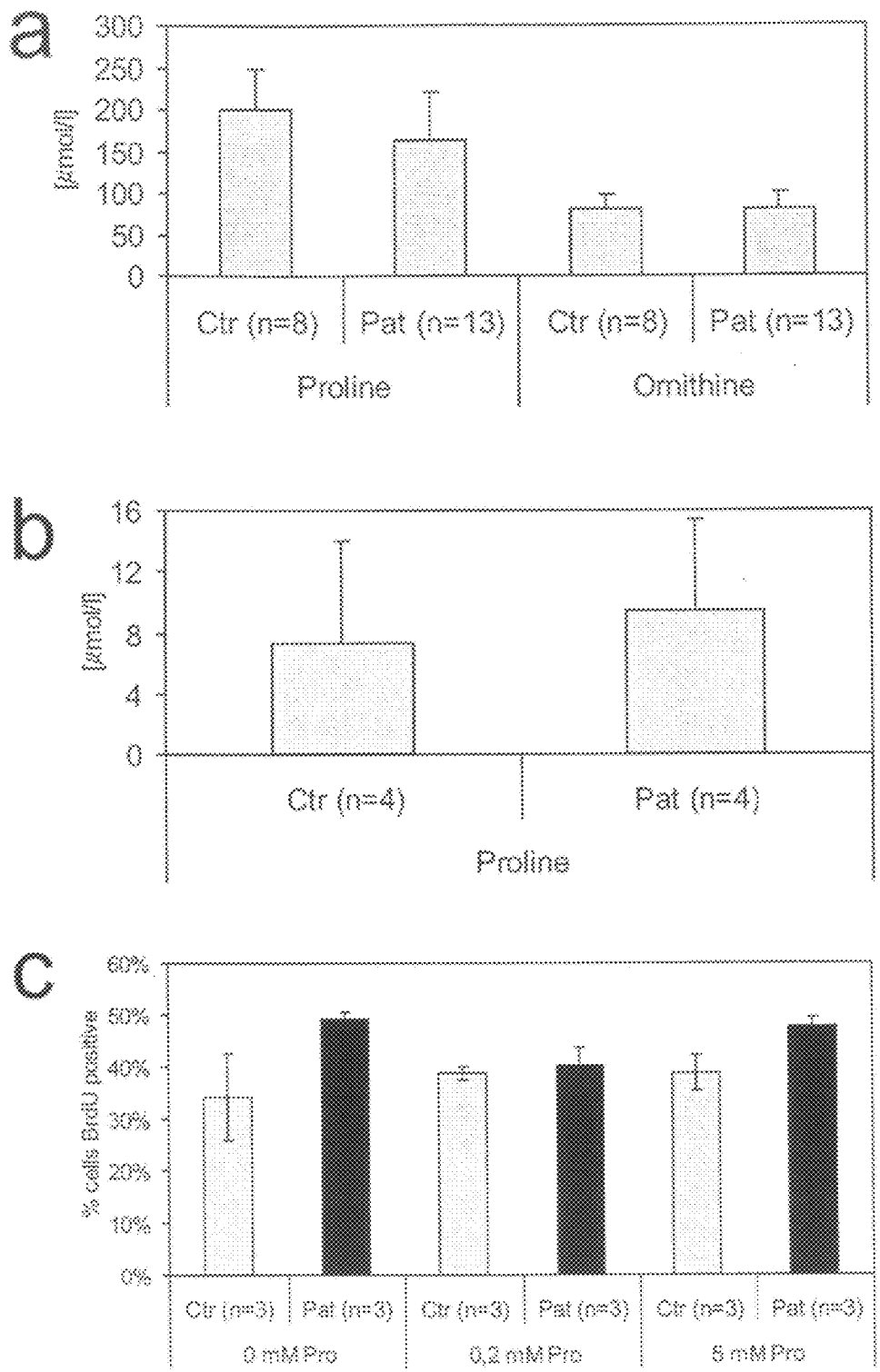
FIG. 8 illustrates proline and ornithine levels in individuals with PYCR1 mutations compared to controls; proline levels in fibroblast lysates from controls and from individuals with PYCR1 mutation; and proliferation rates of fibroblasts from individuals with PYCR1 mutations and controls.

FIG. 8 a) Proline and ornithine levels in individuals with PYCR1 mutations (Pat) compared to controls (Ctr). Note non-significant (p=0.051) reduction of proline concentrations in affected individuals. b) Proline levels in fibroblast lysates from controls and from individuals with PYCR1 mutation. No significant differences were detectable. c) Proliferation rates of fibroblasts from individuals with PYCR1 mutations (Pat) and controls (Ctr) grown in medium with different proline concentrations. No significant differences were observed, but mutant cells showed slightly higher proliferation. Representative result of two independent experiments. Ctr=control; Pat=patent.

FIG. 9 Partial rescue of the Pycr1 morphant phenotype by overexpression of human wild-type Pycr1 mRNA but not mutant Pycr1 K215-D319del mRNA. (a) Control tadpole at stage 42. (b) Pycr1-depleted tadpole. (c) tadpole injected with 800 pg of synthetic mRNA of wild-type human Pycr1. (d) Pycr1-depleted tadpole injected with 800 pg of synthetic mRNA of wild-type human Pycr1, note the rescued stunted growth relative to b. (e) Injection of 800 pg of synthetic mRNA of mutant K215-D319del human PYCR1 is without effect. (f) Stunted growth of Pycr1-depleted tadpole is not rescued by injection of 800 pg of synthetic mRNA of mutant K215-D319del human PYCR1.

Figure 10:
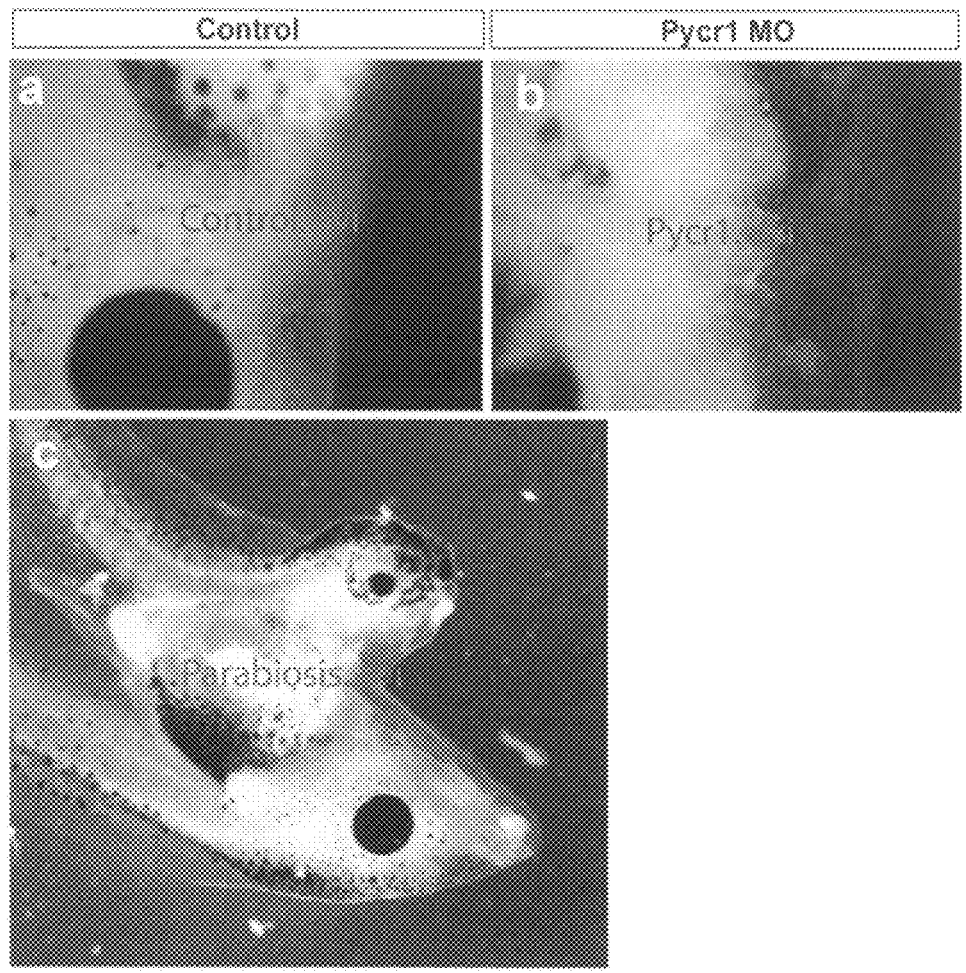
FIG. 10 illustrates tadpoles and hearts of tadpoles showing that blood defects in Pycr1 morphants are alleviated by parabiosis.

FIG. 10 Blood defects in Pycr1 morphants are alleviated by parabiosis. (a) Movie of Circulating red blood cells and beating heart in control tadpole at stage 30. (b) Movie of beating heart in Pycr1 morphant tadpole at stage 30 despite absence of circulating red blood cells. (c) Movie of shared blood circulation between Pycr1 morphant (top) and control tadpole (bottom) in parabiotic embryos at stage 45.

Figure 11:
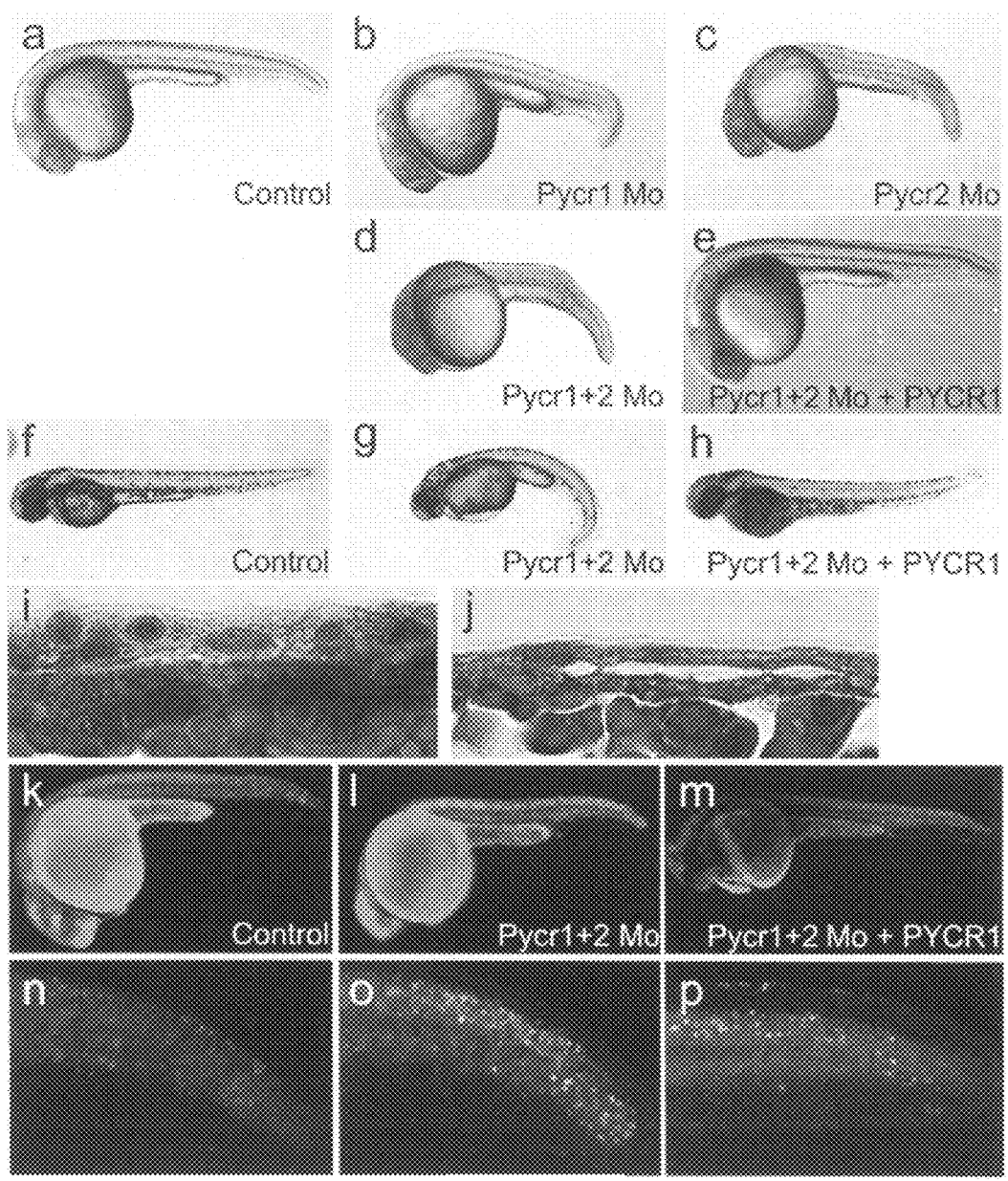
FIG. 11 illustrates zebrafish, epidermis of zebrafish, and zebrafish cells showing that the knockdown of Pycr1 and Pycr2 in zebrafish leads to malformation, epidermal atrophy and increased apoptosis.

FIG. 11 Knockdown of Pycr1 and Pycr2 in zebrafish leads to malformation, epidermal atrophy and increased apoptosis. (a-h) Control, Pycr1 morphant, Pycr2 morphant, Pycr1+2 morphant and Pycr1+2 morphant zebrafish injected with 20 pg human PYCR1 mRNA at stage 24 h. (f-h) Control, Pycr1+2 morphant and Pycr1+2 morphant zebrafish injected with 20 pg human PYCR1 mRNA at stage 48 hours. Note reduced length of morphant fishes, abnormally bowed tail and loosening of the epidermis around the yolk sac. The severity of the phenotype increases when Pycr1 and Pycr2 are both knocked down. Only subtle changes are seen after rescue of the morphant phenotype with 20 pg of human PYCR1 mRNA. (iJ) Dermal atrophy in Pycr1+2 morphants. In 48 hours-old control fish (i) a double-layered epidermis surrounds the yolk sac. In Pycr1+2 morphants this epidermis is atrophic. Goldner trichrome staining. (k-m) Acridine orange staining of apoptotic cells at stage 24 h. Note significant increased number of apoptotic cells in morphants and almost complete reversion of the phenotype by co-injection of the human PYCR1 mRNA. (n-p) Acridine staining of apoptotic cells in the tail, higher magnification.

FIG. 12 shows the amino acid sequence of PYCR1 gene (Swiss Prot Accession No. P32322).

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

The following references are cited within the specification
1. Kielty, C. M. Elastic fibres in health and disease. *Expert Rev Mol Med* 8, 1-23 (2006).
2. Zhang, M. C. et al. Cutis laxa arising from frameshift mutations in exon 30 of the elastin gene (ELN). *J Biol Chem* 274, 981-6 (1999).
3. Megarbane, H. et al. An Autosomal-Recessive Form of Cutis Laxa Is Due to Homozygous Elastin Mutations, and the Phenotype May Be Modified by a Heterozygous Fibulin 5 Polymorphism. *J Invest Dermatol* (2009).
4. Hucthagowder, V. et al. Fibulin-4: a novel gene for an autosomal recessive cutis laxa syndrome. *Am J Hum Genet* 78, 1075-80 (2006).
5. Loeys, B. et al. Homozygosity for a missense mutation in fibulin-5 (FBLN5) results in a severe form of cutis laxa. *Hum Mol Genet* 11, 2113-8 (2002).
6. Hennies, H. C. et al. Gerodermia osteodysplastica is caused by mutations in SCYL1BP1, a Rab-6 interacting golgin. *Nat Genet* 40, 1410-2 (2008).
7. Kornak, U. et al. Impaired glycosylation and cutis laxa caused by mutations in the vesicular H+-ATPase subunit ATP6V0A2. *Nat Genet* 40, 32-4 (2008).

8. de Barsy, A. M., Moens, E. & Dierckx, L. Dwarfism, oligophrenia and degeneration of the elastic tissue in skin and cornea. A new syndrome? *Helv Paediatr Acta* 23, 305-13 (1968).
9. Van Maldergem, L. et al. Cobblestone-like brain dysgenesis and altered glycosylation in congenital cutis laxa, Debre type. *Neurology* 71, 1602-8 (2008).
10. Kivuva, E. C., Parker, M. J., Cohen, M. C., Wagner, B. E. & Sobey, G. De Barsy syndrome: a review of the phenotype. *Clin Dysmorphol* 17, 99-107 (2008).
11. Al-Gazali, L. I., Sztriha, L., Skaff, F. & Haas, D. Gerodermia osteodysplastica and wrinkly skin syndrome: are they the same? *Am J Med Genet* 101, 213-20 (2001).
12. Hamamy, H., Masri, A. & Ajlouni, K. Wrinkly skin syndrome. *Clin Exp Dermatol* 30, 590-2 (2005).
13. Nanda, A. et al. Gerodermia osteodysplastica/wrinldy skin syndrome: report of three patients and brief review of the literature. *Pediatr Dermalol* 25, 66-71 (2008).
14. Kunze, J. et al. De Barsy syndrome—an autosomal recessive, progeroid syndrome. *Eur J Pediatr* 144, 348-54 (1985).
15. Rajab, A. et al. Geroderma Osteodysplasticum and Wrinkly Skin Syndrome in 22 patients from Oman. *Am J Med Genet* (in press) (2008).
16. Guerra, D. et al. The De Barsy syndrome. *J Cutan Pathol* 31, 616-24 (2004).
17. Martin, G. M. Genetic modulation of senescent phenotypes in *Homo sapiens*. *Cell* 120, 523-32 (2005).
18. Mitsubuchi, H., Nakamura, K., Matsumoto, S. & Endo, F. Inborn errors of proline metabolism. *J Nutr* 138, 2016S-2020S (2008).
19. Baumgartner, M. R. et al. Delta1-pyrroline-5-carboxylate synthase deficiency: neurodegeneration, cataracts and connective tissue manifestations combined with hyperammonaemia and reduced ornithine, citrulline, arginine and proline. *Eur J Pediatr* 164, 31-6 (2005).
20. Bicknell, L. S. et al. A missense mutation in ALDHI18A1, encoding Delta1-pyrroline-5-carboxylate synthase (P5CS), causes an autosomal recessive neurocutaneous syndrome. *Eur J Hum Genet* 16, 1176-86 (2008).
21. Baumgartner, M. R et al. Hyperammonemia with reduced ornithine, citrulline, arginine and proline: a new inborn error caused by a mutation in the gene encoding delta(1)-pyrroline-5-carboxylate synthase. *Hum Mol Genet* 9, 2853-8 (2000).
22. Hucthagowder, V. et al. Loss-of-Function Mutations in ATP6V0A2 Impair Vesicular Trafficking, Tropoelastin Secretion, and Cell Survival. *Hum Mol Genet* (2009).
23. Krishnan, N., Dickman, M. B. & Becker, D. F. Proline modulates the intracellular redox environment and protects mammalian cells against oxidative stress. *Free Radic Biol Med* 44, 671-81 (2008).
24. Phang, J. M., Pandhare, J. & Liu, Y. The metabolism of proline as microenvironmental stress substrate. *J Nutr* 138, 2008S-2015S (2008).
25. Hagedorn, C. H. & Phang, J. M. Transfer of reducing equivalents into mitochondria by the interconversions of proline and delta 1-pyrroline-5-carboxylate. *Arch Biochem Biophys* 225, 95-101 (1983).
26. Meng, Z. et al. Crystal structure of human pyrroline-5-carboxylate reductase. *J Mol Biol* 359, 1364-77 (2006).
27. Balaban, R. S., Nemoto, S. & Finkel, T. Mitochondria, oxidants, and aging. *Cell* 120, 483-95 (2005).
28. Abecasis, G. R., Cherny, S. S., Cookson, W. O. & Cardon, L. R. Merlin—rapid analysis of dense genetic maps using sparse gene flow trees. *Nat Genet* 30, 97-101 (2002).
29. Thiele, H I. & Nurnberg, P. HaploPainter: a tool for drawing pedigrees with complex haplotypes. *Bioinformatics* 21, 1730-2 (2005).
30. Hensey, C. & Gautier, J. Programmed cell death during *Xenopus* development: a spatio-temporal analysis. *Dev Biol* 203, 36-48 (1998).
31. Picoult-Newberg L., et al, Mining SNPs from EST databases, *Genome Res.* 9 (1999) 167-174
32. Altshuler D. et al., An SNP map of human genome generated by reduced representation shotgun sequencing, *Nature* 407 (2000) 513-516.
33. U.S. Pat. No. 5,432,272
34. U.S. Pat. No. 6,143,877
35. U.S. Pat. No. 6,127,121
36. U.S. Pat. No. 4,677,968

What is claimed is:

1. A method of identifying a compound capable of modifying the activity of a pyrroline-5-carboxylate reductase 1 (PYCR1) mutein, the method comprising:
 a. contacting a skin layer with a compound of interest wherein skin cells of the skin layer comprise a PYCR1 mutein and/or a nucleic acid molecule encoding a mutein of PYCR1, and
 b. measuring the expression of the PYCR1 mutein, the expression of the PYCR1 gene encoding for the PYCR1 mutein, or both, and
 c. comparing the result of the measurement obtained from step (b) with that of a control measurement without the addition of the compound of interest,
wherein the compound increases the expression of the PYCR1 mutein and/or the PYCR1 gene encoding for the PYCR1 mutein in the presence of the compound compared to the control indicating that the compound of interest has a desired property and wherein the PYCR1 mutein comprises or consists of the amino acid sequence set forth in SEQ ID NO. 4, wherein the amino acid residue corresponding to sequence position 206 is mutated.

2. The method according to claim 1 wherein the PYCR1 mutein is expressed in an isolated skin flap comprising at least one layer of living animal skin, said flap being attached to a test animal; and the compound of interest is contacted by applying the compound to the living animal skin.

3. The method according to claim 2, wherein the skin flap comprises living human skin on one surface and living animal skin on another surface.

4. The method according to claim 2, wherein the skin flap is being served by an isolated vasculature attached to the test animal.

5. The method according to claim 2, further comprising removing at least one sample of blood, wherein the contents of the blood removed is being analysed.

6. The method according to claim 2, further comprising obtaining a sample of DNA from the skin flap to measure the expression of the PYCR1 gene encoding for the PYCR1 mutein.

7. The method according to claim 2, wherein the living animal skin is of the same or different species than the test animal.

8. The method according to claim 2, wherein the test animal is a mammal.

9. The method according to claim 2, wherein the test animal is a human or a rodent.

10. The method according to claim 2, wherein the test animal is selected from the group consisting of mouse, rat, squirrel, chipmunk, gopher, porcupine, beaver, hamster, gerbil, guinea pig, chinchilla, prairie dog, and groundhog.

11. The method according to claim 2, wherein the test animal is an athymic rodent.

12. The method according to claim 2, wherein the compound of interest is formulated in a form of a cosmetic composition.

13. The method according to claim 12, wherein the cosmetic composition is selected from the group consisting of gels, ointment, cream, lotion, serum, pastes, soaps, aerosols, soluble tablets, powder, sticks, water-based or oil-based suspensions and emulsions.

14. The method according to claim 1, wherein the PYCR1 mutein is expressed in fibroblasts.

15. The method according to claim 1, wherein the amino acid residue at sequence position 206 is replaced by an aromatic amino acid.

16. The method according to claim 15, wherein the aromatic amino acid is selected from the group consisting of phenylalanine, tyrosine and tryptophan.

17. The method according to claim 1, wherein the amino acid residue at sequence position 206 is replaced by a positively charged amino acid.

18. The method according to claim 17, wherein the positively charged amino acid is arginine or lysine.

* * * * *